US007790182B2

(12) United States Patent
Hooper et al.

(10) Patent No.: US 7,790,182 B2
(45) Date of Patent: Sep. 7, 2010

(54) PROTEIN VACCINES AGAINST POXVIRUSES

(75) Inventors: Jay W. Hooper, New Market, MD (US); Genoveffa Franchini, Washington, DC (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 177 days.

(21) Appl. No.: 11/523,867

(22) Filed: Sep. 20, 2006

(65) Prior Publication Data

US 2010/0196491 A1 Aug. 5, 2010

Related U.S. Application Data

(60) Provisional application No. 60/722,082, filed on Sep. 21, 2005.

(51) Int. Cl.
*A61K 39/275* (2006.01)
*A61K 39/285* (2006.01)
*A61K 31/7088* (2006.01)

(52) U.S. Cl. .................................. 424/232.1; 514/44 R
(58) Field of Classification Search ........................ None
See application file for complete search history.

(56) References Cited

U.S. PATENT DOCUMENTS

| | | | | |
|---|---|---|---|---|
| 6,340,463 | B1 | 1/2002 | Mitchell et al. | 424/263.1 |
| 6,451,309 | B2 | 9/2002 | Hooper et al. | 424/147.1 |
| 6,562,376 | B2 * | 5/2003 | Hooper et al. | 424/489 |
| 6,620,412 | B2 | 9/2003 | Hooper et al. | 424/147.1 |
| 6,630,144 | B1 | 10/2003 | Hart et al. | 424/159.1 |

FOREIGN PATENT DOCUMENTS

WO        WO 00/00617        1/2000

OTHER PUBLICATIONS

Doria-Rose et al (Methods 31: 207-216, 2003).*
Shchelkunov et al (Virology 297:172-194, 2002).*
CDC Smallpox Response Plan. Executive summary. Mar. 20, 2003. Centers for Disease Control and Prevention, 1600 Clifton Rd, Atlanta, GA 30333, USA.*
CDC Monkeypox Guidelines and Respources. Jun. 25, 2003. Centers for Disease Control and Prevention, 1600 Clifton Rd, Atlanta, GA 30333, USA.*
Hooper et al (Journal of Virology 78:4433-4443, 2004, cited in IDS).*
Heraud et al (Journal of Immunology 177:25552-2564, 2006, not prior art, cited in IDS).*
Aldaz-Carroll, et al., "Epitope-Mapping Studies Define Two Major Neutralization Sites on the Vaccinia Virus Extracellular Eveloped Virius Glycoprotein B5R", J. Virology, vol. 79, No. 10, May 2005, pp. 6260-6271.
Boyce et al., "Mucosal immune response to trivalent live attenuated intranasal influenza vaccine in children", Vaccine 18 (2000), pp. 82-88.
Chakrabarti et al., "Compact, synthtic, vaccinia virus early/late promoter for protein expression", Short Technical Reports, Biotechniques, vol. 23, No. 6, 1997, pp. 1094-1097.
Chen et al., "Chimpanzee/human mAbs to vaccinia virus B5 protein neutralize vaccinia and smallpox viruses and protect mice against vaccinia virus", PNAS, Feb. 7, 2006, vol. 103, No. 6, pp. 1882-1887.
Czerny and Mahnel, "Structural and functional analysis of orthopoxvirus epitopes with neutralizing monoclonal antibodies", J. General Virology (1990), vol. 71, pp. 2341-2352.
Fang et al. "Immunization with a single extracellular enveloped virus protein produced in bacteria provides partial protection from a lethal orthopoxvirus infection in a natural host", Virology 345 (2006), pp. 231-243.
Fenner, "Poxviruses", chapter 84, Fields Virology, 3rd ed., Lippincott-Raven Publishers, Philadelphia, 1996, pp. 2673-2702.
Fogg et al., "Protective immunity to vaccinia virus induced by vaccination with multiple recombinant outer membrane proteins of intracellular and extracellular virions," J. Virology, vol. 78, No. 19, Oct. 1994, pp. 10230-10237.
Demkowicz et al., "Identification and characterization of vaccinia virus genes encoding proteins that are highly antigenic in animals and are immunodominant in vaccinated humans", J. Virology, vol. 66, No. 1, Jan. 1992, pp. 386-398.
Earl et al., "Immunogenicity of a highly attenuated MVA smallpox vaccine and protection against monkeypox," Nature, vol. 428, Mar. 2004, pp. 182-185.
Edghill-Smith et al., "Smallpox vaccine does not protect macaques with AIDS from a lethal monkeypox virus challenge", JID 2005:191 (Feb. 1), pp. 372-381. Edghill-Smith et al., "Smallpox vaccine-induced antibodies are necessary and sufficient for protection against monkeypox virus", Nature Medicine, vol. 11, No. 7, Jul. 2005, pp. 740-747.
Edghill-Smith et al.,"Modeling a safer smallpox vaccination regimen, for human immunodeficiency virus type 1-infected patients, in immunocompromised macaques", JID 2003:188 (Oct. 15), pp. 1181-1191.
Engelstad et al., "A constitutively expresses vaccinia gene encodes a 42-kDa glycoprotein related to complement control factors that forms part of the extracelllular virus envelope", Virology 188, pp. 801-810 (1992).
Esposito et al., "Genome sequence diversity and clues to the evolution of variola (smallpox) virus", Science, vol. 313, Aug. 11, 2006, pp. 807-812.
Galmiche et al., "Neutralizing and protective antibodies directed against vaccinia virus envelope antigens", Virology 254, (1999), pp. 71-80.
Gordon et al., "A prominent antigenic surface polypeptide involved in the biogenesis and function of the vaccinia virus envelope", Virology 181, (1991), pp. 671-686.

(Continued)

*Primary Examiner*—Mary E Mosher
(74) *Attorney, Agent, or Firm*—Elizabeth Arwine

(57) ABSTRACT

The invention described here entails a protein vaccine against poxviruses which contains at least two purified recombinant monkeypox virus proteins or peptides. The proteins or peptides are encoded by the open reading frames of the monkeypox ortholog genes M1R, A35R, A29L B6R, and orthologs of these proteins or peptides having 90% identity. The invention also entails a vaccine protocol against poxvirus whereby a vaccine is vaccinated with a first vaccine made up of a nucleic acid vaccine of three or more poxvirus virus genes, and subsequently vaccinated with at least one other booster vaccine made up of two or more poxvirus virus proteins.

14 Claims, 17 Drawing Sheets

OTHER PUBLICATIONS

Hammarlund et al., "Multiple diagnostic techniques identify previously vaccinated individueals with protective immunity against monkeypox", Nature Medicine, vol. 11, No. 9, Sep. 2005, pp. 1005-1011.

Herrera at al., "Functional analysis of vaccinia virus B5R protein: essential role in virus envelopment is independent of a large portion of the extracellular domain", J. Virology, Jan. 1998, vol. 72, No. 1, pp. 294-302.

Hooper et al., (Abstract P23-6) "DNA immunization with the vaccinia L1R and/or A33R genes", poster at meeting for American Society for Virology, Jul. 1998, p. 190.

Hooper et al., (Abstract W33-5) "DNA vaccination against poxviruses using combinations of IMV and EEV immunogens" poster at meeting for American Society for Virology, Jul. 2000, p. 113.

Hooper et al., "DNA vaccination with vaccinia virus L1R and A33R genes protects mice against a lethal poxvirus challenge", Virology 266, (2000), pp. 329-339.

Heraud, et al., "Subunit recombinant vaccine protects against monkeypox", J. Immunology, 2006, pp. 2552-2564.

Hooper et al., "Smallpox DNA vaccine protects nonhuman primates against lethal monkeypox", J. Virology, May 2004, vol. 78, No. 9, pp. 4433-4443.

Hooper et al.,"Four-gene-combination DNA vaccine protects mice against a lethal vaccinia virus challenge and elicits appropriate antibody responses in nonhuman primates", Virology 306 (2003), pp. 181-195.

Hutin et al, "Outbreak of human monkeypox, Democratic Republic of Congo, 1996-1997", Emerging Infectious Diseases, vol. 7, No. 3, May-Jun. 2001, pp. 434-438.

Ichihashi et al, "Identification of a vaccinia virus penetration protein", Virology 202, 1994, pp. 834-843.

Ichihashi et al., "Neutralizing epitope on penetration protein of vaccinia virus", Virology 220, (1996), pp. 491-494.

Isaacs et al., "Characterization of a vaccinia virus-encoded 42-kilodalton Class I membrane glycoprotein component of the extracellular virus envelope", J. Virology, vol. 66, No. 12, Dec. 1992, pp. 7217-7224.

Kemper et al., "Expected adverse events in a mass smallpox vaccination campaign", Effective Clinical Practice, Mar./Apr. 2002, www.acponline.org/journals/ecp/marapr02/kemper.htm , 9 pages.

Kulesh et al., "Smallpox and pan-orthopox virus detection by real-time 3'-minor groove binder TaqMan assays on the Roche LightCycler and the Cepheid Small Cycler platforms", J. Clinical Microbiology, Feb. 2004, vol. 42, No. 2, pp. 601-609.

Lai et al., "The purified 14-kilodalton envelope protein of vaccinia virus produced in *Escherichia coli* induces virus immunity in animals", J. Virology, Oct. 1991, vol. 65, No. 10, pp. 5631-5635.

Law and Smith, "Antibody neutralization of the extracellular enveloped form of vaccinia virus", Virology 280, 2001, pp. 132-142.

Lin et al., "Vaccinia virus envelope H3L protein binds to cell surface heparan sulfate and is important for intracellular mature virion morphogenesis and virus infection in vitro and in vivo", J. Virology, Apr. 2000, vol. 74, No. 7, pp. 3353-3365.

Manischewitz et al., "Development of a novel vaccinia-neutralization assay based on reporter-gene expression", JID 2003:188 (Aug. 1), pp. 440-448.

Maruyama et al., "Recombinant human monoclonal antibodies to Ebola virus", JID 1999:179 (suppl. 1) S235-9.

Mercer et al., "A novel strategy for determining protective antigens of the parapoxvirus, Orf virus", Virology 229, (1997), pp. 193-200.

Mercer et al. (Abstract from Medline), "Lack of cross-protection between vaccinia virus and orf virus in hysterectomy-procured, barrier-maintained lambs", PMID:7801537, Aug. 15, 1994 (4), pp. 373-382.

Meyer et al., "Outbreakes of disease suspected of being due to human Monkeypox virus infection in the Democratic Republic of Congo in 2001", J. Clinical Microbiology, Aug. 2002, vol. 40, No. 8, pp. 2919-2921.

Meyer et al., "Identification of binding sites for neutralizing monoclonal antibodies on the 14-kDa fusion protein of orthopox viruses", Short Communication, Virology 200, pp. 778-783 (1994).

CDC. 2001. Vaccinia (smallpox) vaccine: recommendations of the Advisory Committee on Immunization Practices (ACIP), 2001. Morb.Mortal.Wkly.Rep. 50:1-26.

CDC. 2003. Multistate outbreak of monkeypox—Illinois, Indiana, and Wisconsin, 2003. Morb.Mortal.Wkly.Rep. 52:537-540.

Moller-Larsen et al.,"Humoral and cell-mediated immune responses in humans before and after revaccination with Vaccinia Virus", Infection and Immunity, vol. 19, No. 1, Jan. 1978, pp. 34-39.

Moss, Bernard, "Poxviridae: The viruses and their replication."Chapter 83 in Fields Virology, Third edition, ed. B.N. Fields et al., Lippincott-Raven Publishers, Philadelphia. 1996. pp. 2637-2671.

Nalca, A., A. W. Rimoin, S. Bavari, and C. A. Whitehouse. 2005. "Reemergence of monkeypox: prevalence, diagnostics, and countermeasures." Clin.Infect.Dis. 41:1765-1771.

Osterhaus, A. D., C. A. van Baalen, R. A. Gruters, M. Schutten, C. H. Siebelink, E. G. Hulskotte, E. J. Tijhaar, R. E. Randall, G. van Amerongen, A. Fleuchaus, V. Erfle, and G. Sutter. 1999. "Vaccination with Rev and Tat against AIDS." Vaccine 17:2713-2714.

Rodriguez et al., "Isolation and characterization of neutralizing monoclonal antibodies to vaccinia virus", Abstract from PubMed online database, 1 page, derived from J. Virol., 1985, 56(2):482-488.

Rodriguez et al., "Mapping and mucletode sequence of the vaccinia virus gene that encodes a 14-kilodalton fusion protein", J. Virology, Nov. 1987, pp. 3550-3554.

Rodriguez et al., "The vaccinia virus 14-kilodalton fusion protein forms a stable complex with the processed protein encoded by the vaccinia virus A17L gene", J. Virology, Jun. 1993, vol. 67, No. 6, pp. 3435-3440.

Roper et al., "Extracellular vaccinia virus envelope glycoprotein encoded by the A33R gene", J. Virology, Jun. 1996, vol. 70, No. 6, pp. 3753-3762.

Saha et al., "BcePred: prediction of continuous B-cell epitopes in antigenic sequences using physico-chemical properties", In ICARIS 2004, LNCS 3239. G. Nicosia, V. Cutello, P. J. Bentley, and J. Timis, eds. Springer, pp. 197-204.

Sanchez et al., "Biochemical analysis of the secreted and virion glycoproteins of Ebola virus", J. Virology, Aug. 1998, vol. 72, pp. 6442-6447.

Sanderson et al., "Teh vaccinia virus A27L protein is needed for the microtubule-dependent transport of intracellular mature virus particles", Abstract from PubMed, 1 page, derived from J. Gen. Virol, 2000, 81 Pt.1:47-58.

CDC. 2003. Supplemental recommendations on adverse events following smallpox vaccine in the pre-event vaccination program: recommendations of the Advisory Committee on Immunization Practices. Morb.Mortal.Wkly.Rep. 52:282-284.

Smith, G. L. and M. Law. 2004. The exit of vaccinia virus from infected cells. Virus Res. 106:189-197.

Snyder, J. T., I. M. Belyakov, A. Dzutsev, F. Lemonnier, and J. A. Berzofsky. 2004. Protection against lethal vaccinia virus challenge in HLA-A2 transgenic mice by immunization with a single CD8+ T-cell peptide epitope of vaccinia and variola viruses. J.Virol. 78:7052-7060.

Vazquez et al., "The vaccinia virus 14-kilodalton (A27L) fusion protein forms a triple coiled-coil structure and interacts wit the 21-kilodalton (A17L) virus membrane protein through a C-terminal alpha-helix", J. Virology, Dec. 1998, vol. 72, No. 12, pp. 10126-10137.

Vazquez etal, "Identification of functional domains in the 14-kilodalton envelope protein (A27L) of vaccinia virus", J. virology, Nov. 1999, vol. 73, No. 11, pp. 9098-9109.

Volchkov et al., "The envelope glycoprotein of Ebola virus contains an immunosuppressive-like domain similar to oncogenic retroviruses", FEBS Letters, vol. 305, No. 3, 1992, pp. 181-184.

Wilson et al., "Epitopes involved in antibody-mediated protection from Ebola virus", Science, Mar. 3, 2000, vol. 2878, pp. 1664-1666.
Wolffe et al., "A myristylated membrane protein encoded by the vaccinia virus L1R open reading frame is the target of potent neutralizing monoclonal antibodies", Virology 211, pp. 53-62 (1995).

Wyatt, L. S., P. L. Earl, L. A. Eller, and B. Moss. 2004. Highly attenuated smallpox vaccine protects mice with and without immune deficiencies against pathogenic vaccinia virus challenge. Proc.Natl. Acad.Sci.U.S.A 101:4590-4595.

Xu et al., "Immuization for Ebola virus infection", Nature Medicine, vol. 4, No. 1, Jan. 1998, pp. 37-42.

Yirrell et al., "Immune responses of patients to orf virus infection", British Journal of Dermatology, 130:438-43, 1994, Abstract from Medline, 1 page.

Zaucha, G. M., P. B. Jahrling, T. W. Geisbert, J. R. Swearengen, and L. Hensley. 2001. The pathology of experimental aerosolized monkeypox virus infection in cynomolgus monkeys (*Macaca fascicularis*). Lab Invest. 81:1581-1600.

Jezek, Z., M. Szczeniowski, K. M. Paluku, and M. Mutombo. 1987. Human monkeypox: clinical features of 282 patients. J.Infect.Dis. 156:293-298.

Jezek, Z., S. S. Marennikova, M. Mutumbo, J. H. Nakano, K. M. Paluku, and M. Szczeniowski. 1986. Human monkeypox: a study of 2,510 contacts of 214 patients. J.Infect.Dis. 154:551-555.

Belyakov et al., 2003, "Shared modes of protection against poxvirus infection by attenuated and conventional smallpox vaccine viruses", Proc. Natl., Acad. Sci. USA 100:9458-9463.

Centers for Disease Control and Prevention. 2003. Update: adverse events following civilian smallpox vaccination—United States, 2003. Morb. Mortal. Wkly. Rep..52:419-420.

Centers for Disease Control and Prevention. 2003. Update: multistate outbreak of monkeypox—Illinois, Indiana, Kansas, Missouri, Ohio, and Wisconvin, 2003. Morb. Mortal. Wkly. Rep. 52:642-646.

Czerny et al. 1990. "Structural and functional analysis of orthopoxvirus epitopes with neutralizing monoclonal antibodies." J. Gen. Virol. 71:2341-2352.

Czerny et al. 1994. "Epitope detection in the envelope of intracellular naked orthopox viruses and identification of encoding genes". Virology 200:764-777.

Dalgaard, J.B., 1957. "Fatal myocarditis following smallpox vaccination." Am. Heart J., 54:156-157.

Fenner etal. 1988. "Smallpox and its eradication", p. 1-68. World Health Organization, Geneva, Switzerland.

Fenner etal. 1988. "Smallpox and its eradication", p. 122-167. World Health Organization, Geneva, Switzerland.

Hammarlund et al. 2003. "Duration of anticiral immunity after smallpox vaccination." Nat.Med. 9:1131-1137.

Hooper et al. 2003. "Four-gene-combination DNA vaccine protects mice against a lethal vaccinia virus challenge and elicits appropriate antibody responses in nonhuman primates", Virology 306:181-195.

Hooper et al. 2001. "DNA vaccination with the Hantaan virus M gene protects hamsters against three of four HFRS hantaviruses and elicits a high-titer neutralizing antibody response in rhesus monkeys", J. Virol. 75:8469-8477.

Ibrahim et al. 2003. "Real0time PCR assay to detect smallpox virus", J. Clin. Microbiol. 41:3835-3839.

Jezek et al. 1988. "Clinical features of human monkeypox", p. 58-80, In J.L. Melnick (ed.), Monographs in Virology, vol. 17, Karger, Basel, Switzerland.

Jezek et al. 1988. "Epidemiology of human monkeypox", p. 81-109, In J.L. Melnick (ed.), Monographs in Virology, vol. 17, Karger, Basel, Switzerland.

Kempe, C.H. 1960. "Studies on smallpox and complications of smallpox vaccination." Pediatrics 25:176-189.

McClain et al., 1997. "Immunologic responses to vaccinia vaccines administered by different parenteral routes." J. Infect. Dis. 175:756-763.

McConnell et al. 1964. "Protection of rhesus monkeys against monkeypox by vaccinia virus immunication." Am.J. Vet. Res. 25:192-195.

Moss, B. 2001. "Poxviridae: the viruses and their replication", 2866-2868. In D. Knipe and P.M. Howley (ed), Fields Virology, 4th ed., vol. 2., Lipincott Williams and Wilkins, Philadelphia, PA.

Prier and Sauer. 1960. "A pox visease of monkeys." Ann. N.Y. Acad. Sci., 85:951-959.

Ramirez et al., 2002. "Administration to mice of a monoclonal antibody that neurtralizes the intracellular mature virus form of vaccinia virus limits virus replication efficiently under prophylactic and therapeutic conditions", J. Gen. Virol. 83:1059-1067.

Rodriguez and Esteban. 1987. "Mapping and nucleotide sequence of the vaccinia virus gene that encodes a 14-kilodalton fusion protein", J. Virol. 61:3550-3554.

Rosenthal et al. 2001. "Developing new smallpox vaccines." Emerg. Infect. Dis. 7:920-926.

Shchelkunov et al. 2002. "Analysis of the monkeypox virus genome." Virology 297:172-194.

Weltzin et al. 2003. "Clonal vaccinia virus grown in cell culture as a new smallpox vaccine", Nat. Med. 9:1125-1130.

Wolffe et al. 1995. "A myristylated membrane protein encoded by the vaccinia virus L1R open reading frame is the target of potent neutralizing monoclonal antibodies", Virology 211:53-63.

Moss, Bernard, "Poxviridae: The Viruses and Their Replication", Chapter 83, Fields Virology, 3rd Edition, B.N. Fields, D.M. Knipe, P.M. Howley et al. (ed), Lippincott-Raven Publishers, Philadelphia, 1996, pp. 2637-2671.

Hollinshead et al., "Vaccinia Virus Intracellular Mature Virions Contain only One Lipid Membrane", J. Virology, vol. 73, No. 2, Feb. 1999, p. 1503-1517.

Schmelz et al.,"Assembly of vaccinia virus: the second wrapping cisterna is derived from the trans golgi network", J. Virology, Jan. 1994, vol. 68, No. 1, pp. 130-147.

Cudmore et al, "Actin-based motility of vaccinis virus," Letters to Nature, Nature, vol. 378, Dec. 7, 1995, pp. 636-638.

Blasco and Moss, "Extracellular vaccinia virus formation and cell-to-cell virus transmission are prevented by deletion of the gene encoding the 37,000-dalton outer envelope protein", J. Virlogy, Nov. 1991, vol. 65, No. 11, pp. 5910-5920.

Payne, Lendon, "Significance of extracellular enveloped virus in the in vitro and in vivo dissemination of vaccinia", J. Gen. Virol. (1980), 50, pp. 89-100.

Gordon et al., "A prominent antigenic surface polypeptide involved in teh biogenesis and function of the vaccinia virus envelope", Virology, 181, pp. 671-686 (1991).

Lai et al., "The purified 14-kilodalton envelope protein of vaccinia virus produced in *Escherichia coli* induces virus immunity in animals", J. Virology, Oct. 1991, vol. 65, No. 10, pp. 5631-5635.

Rodriguez and Esteban, "Mapping and nucleotide sequence of the vaccinia virus gene that encodes a 14-kilodalton fusion protein", J. Virology, Nov. 1987, vol. 61, No. 11, pp. 3550-3554.

Hsiao et al., "Vaccinia virus envelope D8L protein binds to cell surface chondroitin sulfate and Mediates the adsorption of intracellular mature virions to cells", J. Virology, Oct. 1999, vol. 73, No. 10, pp. 8750-8761.

Ichihashi et al., "Identification of a vaccinia virus penetration protein", Virology 202, pp. 834-843 (1994).

McConnell et al., "Protection of Rhesus Monkeys Against Monkeypox by Vaccinia Virus Immunization", Am. J. Vet. Res., Jan. 1964, vol. 25, pp. 192-195).

Golden and Hooper, "Heterogeneity in the A33 protein impacts the cross-protective efficacy of a candidate smallpox DNA vaccine.", Virology. Jul. 20, 2008;377(1):19-29. Epub May 14, 2008.

Aldaz-Carroll et al., "Major neutralizing sites on vaccinia virus glycoprotein B5 are exposed differently on variola virus ortholog B6." J Virol. Aug. 2007;81(15):8131-9. Epub May 23, 2007.

Su et al., "Structural basis for the binding of the neutralizing antibody, 7D11, to the poxvirus L1 protein." Virology. Nov 25, 2007;368(2):331-41. Epub Aug. 3, 2007.

Buller and Wallace, "Reexamination of the efficacy of vaccination against mousepox.", Lab Anim Sci. Oct. 1985;35(5):473-6.

Sakhatskyy et al., "Immunogencity and protection efficacy of subunit-based smallpox vaccines using variola major antigens", Virology 371 (2008) pp. 98-107.

* cited by examiner

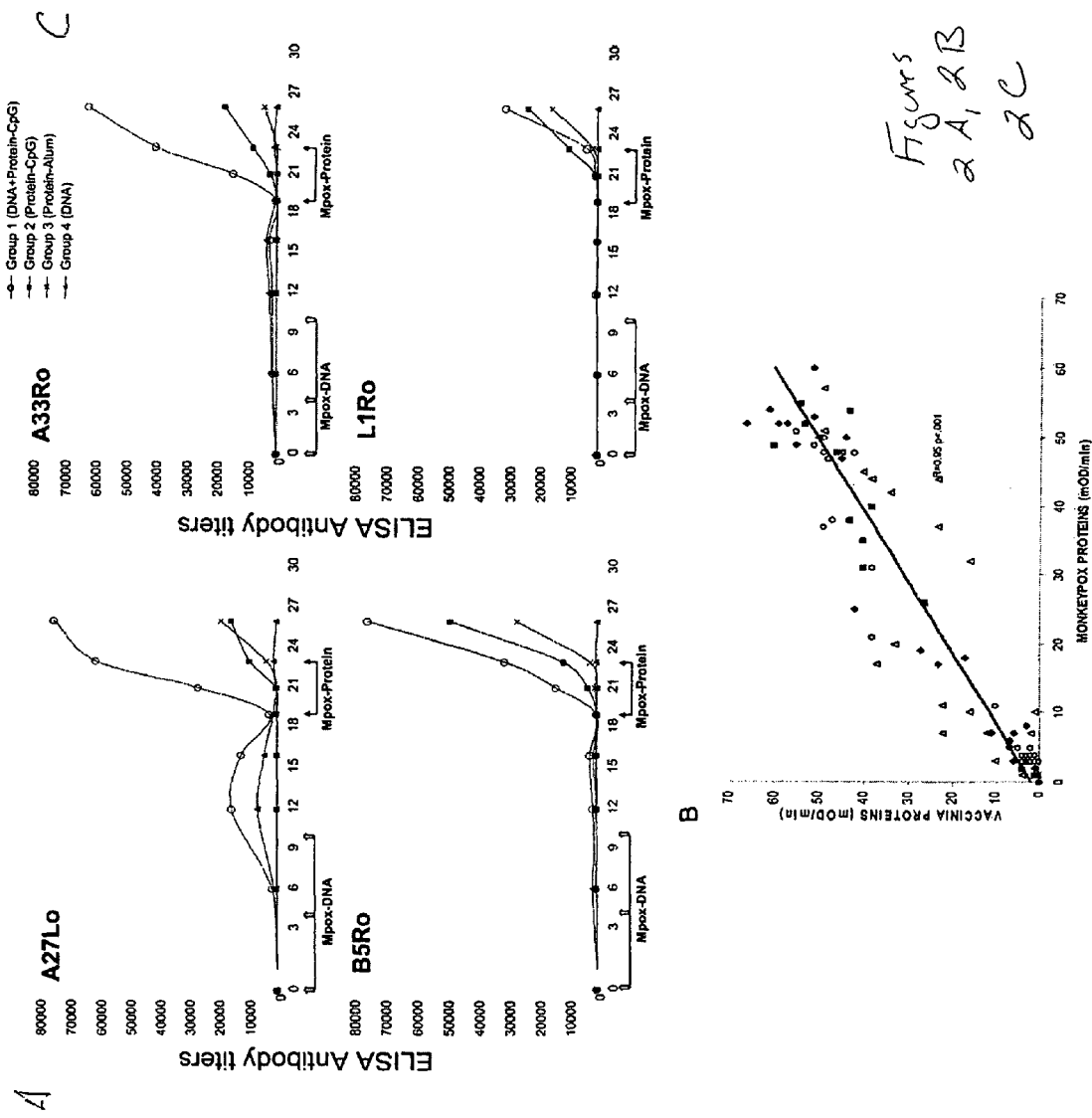

High-titer neutralizing antibody response against monkeypox virus and vaccinia virus after 1 DNA vaccination followed by 2 protein vaccination booster

| Group | Animal | Week 9 (4 weeks after 2nd vaccination) MPOV PRNT50 GMT | Week 14 (3 wks after 3rd vaccination) MPOV PRNT50 GMT | Week 14 (3 wks after 3rd vaccination) VACV PRNT50 GMT | Week 33 (22 wks after 3rd vaccination) VACV PRNT50 |
|---|---|---|---|---|---|
| 1 | M549 | < | < | 113 | < |
|   | M551 | < | < | < | < |
|   | M555 | < | < | < | < |
| 2 | M558 | 28 | 640 | 2560 | 320 |
|   | M560 | < | 640 | 2560 | 320 |
|   | M562 | < | 905 | 5120 | 80 |
| 3 | M594 | < | < | < |  |
|   | M596 | < | < | < |  |
|   | M597 | < | < | < |  |
| 4 | M599 | < | < | < |  |
|   | M600 | 28 | < | 57 |  |
|   | M604 | < | < | < |  |
| 5 | M280 | < | < | < |  |
|   | M548 | < | < | < |  |
|   | M585 | < | < | < |  |

MPOV= monkeypox virus Z-79
VACV- vaccinia virus, strain IHD-J
PRNT50= Plaque reduction neutralization test measuring lowest highest dilution neutralizing 50% of the plaques
GMT= geometeric mean titer
All assays were performed in duplicate, either within the same experiment or as an independent experiment.

Figure 10

ELISA data (titers) showing antibody responses against the four vaccine immunogens after a single DNA followed by a protein boost (see group 2 week 9). There are very high ELISA titers after the 2nd protein boost (see group 2 week 14)

| Group | Animal | B5Ro Prebleed | B5Ro Week 9 | B5Ro Week14 | A33Ro Prebleed | A33Ro Week 9 | A33Ro Week14 | A27Lo Prebleed | A27Lo Week 9 | A27Lo Week14 | L1Ro Prebleed | L1Ro Week 9

PROTEIN VACCINES AGAINST POXVIRUSES

This application claims the benefit of priority from provisional application No. 60/722,082, filed Sep. 21, 2005, and the entire contents of that application are incorporated herein by reference.

Viruses in the family Poxyiridae, including vaccinia virus (VACV), variola virus (smallpox), and monkeypox virus, are characterized by a large linear double-stranded DNA genome (130-300 kb) packaged in a relatively large virion (.about.350.times.270 nm), and a cytoplasmic site of replication (reviewed by Moss, 1996, In "Fields Virology", D. M. Knipe et al. Eds., vol. 3, pp 2637-2671. Lippincott-Raven, Philadelphia). Assembly of VACV virions begins with condensation of dense granular material into membrane-wrapped particles called intracellular mature virions (IMV). Recent findings indicate the IMV are wrapped by a single membrane (Hollingshead et al., 1999, J. Virol. 73, 1503-1517) rather than a double membrane as previously reported. IMV are then enveloped in two additional membranes derived from the trans Golgi to form multiple membrane-wrapped particles called intracellular enveloped virions (IEV) (Schmelz et al., 1994, J. Virol. 68, 130-147). IEV are moved, possibly by actin polymerization (Cudmore et al., 1995, Nature 378, 636-638), to the cell periphery, where the outermost membrane fuses with the cell plasma membrane, exposing a cell-associated enveloped virion (CEV) (Blasco and Moss, 1991, J. Virol. 65, 5910-5920). CEV are released from the cell as extracellular enveloped virions (EEV), which play a role in long-range spread of the virus (Payne, 1980, J. Gen. Virol. 50, 89-100). IMV released from disrupted cells and EEV are both infectious forms of VACV.

Smallpox and monkeypox are caused by closely related orthopoxviruses, variola virus and monkeypox virus, respectively. While smallpox is highly transmissible among humans and causes death in approximately one-third of infected individuals, monkeypox is transmitted less efficiently and has a lower mortality rate (see reference citations 1, 2). Smallpox has been eradicated worldwide and it is not a public health concern except for its possible use as a bioterrorism threat. Outbreaks of monkeypox have often been reported in Africa since 1970 (3, 4) and, unexpectedly, in the U.S. (5, 6). The U.S. outbreak (thirty-seven confirmed cases within a few weeks) was due to exposure to monkeypox-infected prairie dogs that had contracted the disease from imported African rodents (5). While an embargo on importation and sale of African rodents would prevent exposure, this episode nevertheless indicates the unpredictable nature of zoonotic infection of humans. Thus, the development of safer vaccines or drugs to prevent or treat such infection will serve the public.

The current smallpox vaccine is a live VACV that has many drawbacks including: adverse reactions, scarring, ocular autoinoculation, dissemination in immunocompromised persons, and dwindling stocks. Adverse events range from the non-serious (e.g., fever, rash, headache, pain, and fatigue) to life-threatening (e.g., exzema vaccinatum, encephalitis, and progressive vaccinia). Serious adverse events that were reported during past and present smallpox vaccination programs include myocarditis and/or myopericarditis. Moreover, live VACV vaccines are problematic because lesion-associated virus at the site of vaccination is infectious and can be inadvertently spread to other parts of the body (e.g., ocular auto-inoculation) and to other individuals (i.e., contact vaccinia). Contact vaccinia has been a significant problem for family members of military vaccines.

Cell culture-derived vaccines are being developed; however, these vaccines are also live viruses and pose many of the same drawbacks that plague the current vaccine. The existing smallpox vaccine Dryvax, a live vaccinia virus (VACV), protects against smallpox and monkeypox, but is contra-indicated in immunocompromised individuals. (7). There are numerous adverse events that can affect both the vaccinee and persons in contact with the vaccinee (e.g., contact vaccinia) (8, 9).

Monkeypox virus infection of healthy rhesus macaques appears to be a suitable model to study protective immune responses against monkeypox (10). Indeed, macaques vaccinated Dryvax are protected from monkeypox (10-14). Recent data have shown that the major mode of protection from monkeypox afforded by the current non-attenuated smallpox vaccine is mediated by antibodies (14). Depletion of either $CD4^+$ T cells or $CD8^+$ T cells in vaccinated animals prior to monkeypox virus challenge does not affect survival, whereas B cell depletion before and during immunization abrogates vaccine-induced protection. Accordingly, passive administration of VACV antibodies confers protection from subsequent lethal monkeypox (14).

The definition of VACV protective antigens has been limited by the complexity of the VACV proteome that encodes some two hundred proteins. Of the approximately 200 genes that comprise the vaccinia genome, only five encode proteins that are known to elicit a neutralizing antibody response including: H3L (Gordon et al., 1991), A27L (Lai et al., 1991; Rodriguez and Esteban 1987), B5R (Galmiche et al., 1999), D8L (Hsiao et al. 1999), and L1R (Ichihashi et al., 1994; Wolffe et al., 1995). Given the structural complexity of VACV, there may be other neutralizing antigens not yet identified. In addition, the A33R gene encodes a protein that elicits a non neutralizing antibody response that is, nevertheless, protective (Schmaljohn unpublished; Galmiche et al., 1999, Virology 254, 71-80).

Nevertheless, proteins L1R and A27L, specific to the intracellular mature virus (IMV), and proteins A33R and B5R, specific to the extracellular enveloped virus (EEV), have been shown to be immunogenic and protected mice from VACV (15-17). In addition, vaccination with a single protein, A33R, was shown to protect against a lethal challenge with ectromelia virus, which is a highly virulent natural pathogen in mice (18). EEV are produced when IMV wrap in additional cellular membranes, move to the cell surface, and release from the cell (19). Both the IMV and EEV forms of poxviruses are infectious. Recently, protection from monkeypox-induced severe disease was also observed following gene gun immunizations with only four VACV DNA plasmids encoding these four proteins (10). U.S. Pat. No. 6,562,376 describes DNA vaccines against poxviruses using IMV and EEV proteins, and this patent is incorporated herein by reference in its entirety.

In light of the problems associated with current live poxvirus vaccines, there is clearly a need for a safe, noninfectious, effective and relatively convenient vaccine alternative that confers protective immunity to poxviruses, which could be used in endemic areas to prevent the suffering caused by diseases such as smallpox.

SUMMARY OF THE INVENTION

Monkeypox transmits poorly from person to person and has a lower rate of mortality (4~15%) (1, 3) compared to smallpox (~30%). However, in contrast to smallpox, monkeypox cannot be eradicated. The virus has an unknown animal reservoir and the existence of more virulent strains is plausible. The 2003 U.S. human monkeypox outbreak (5) was the first to be seen outside Africa; however, cases have continued to occur in central Africa in the decades following the cessation of smallpox vaccination.

The live vaccine (Dryvax) that has eradicated smallpox worldwide poses serious side effects in a subset of people with acquired or congenital defects in the immune system. Moreover, the live virus vaccine is infectious and can be transmitted from the vaccinee to close contacts, including children and persons with weakened immune systems. Thus, vaccination was halted in the late nineteen seventies as it was perceived that the risks of vaccination outweighed its benefits, in the absence of a known smallpox threat. Recent sociopolitical changes worldwide however have raised concerns about the possibility of a deliberate introduction of smallpox in humans. As Dryvax is a replicating vaccine strain and a mass vaccination with it could result in serious adverse effects for high-risk individuals (29), efforts were devoted to the development of safer attenuated smallpox vaccines. MVA and NYVAC, both VACV derivatives, have been shown to be safe in immune-compromised macaques (14, 30) and both can protect immune-competent macaques from lethal monkeypox virus challenge (11) (unpublished results).

There is evidence that the humoral response to vaccination is a necessary and sufficient component of smallpox vaccine-mediated protective immunity. Antibodies play a pivotal role in protection from monkeypox (14); therefore, live poxvirus vectors may not be needed if a subunit vaccine can elicit antibodies that protect macaques against monkeypox. The inventors obtained the proof of principle that indeed it is possible to induce protective antibody responses using recombinant DNA and proteins. Interestingly, DNA alone when delivered by needle injection, or proteins alone did not confer acceptable protection, whereas the combination of DNA and proteins did.

The inventors have developed poxvirus vaccines and immunogenic compositions useful in connection with poxviruses including vaccinia virus, variola virus (smallpox), monkeypox virus and other orthopoxviruses, and virtually any poxvirus having 90% amino acid sequence identity for any of the L1R, A33R, B5R or A27L gene product at the amino acid level. In particular, it is preferable that a vaccine against infection by vaccinia virus include two, three or more of the peptide products of the VACV genes L1R, A33R, A27L and B5R; a vaccine against infection by monkeypox virus include two, three or more of the monkeypox virus orthologs of the peptide products of the VACV genes L1R, A33R, A27L and B5R; a vaccine against infection by variola virus include two, three or more of the variola virus orthologs of the peptide products of the VACV genes L1R, A33R, A27L and B5R, etc. Thus, in one embodiment it is preferred that a vaccine for a poxvirus has two, three or more of the particular poxvirus orthologs of the peptide products of the VACV genes L1R, A33R, A27L and B5R, as long as the poxvirus shares 90% amino acid sequence identity of any of the L1R, A33R, A27L or B5R gene products.

However, due to the high homology between poxviruses, and orthopoxviruses in particular, where the poxvirus has orthologs of the L1R, A33R, A27L or B5R genes (or as described below, orthologs to the corresponding monkeypox virus M1R, A35R, A29L or B6R gene), and those orthologs produce proteins/peptides that share 90% identity with the amino acid sequence of the gene products of two, three or more of the L1R, A33R, A27L or B5R genes (or as described below, gene products of the monkeypox virus M1R, A35R, A29L or B6R gene), those poxvirus ortholog gene products may be used as vaccine components for other poxviruses—as long as those other poxviruses themselves have orthologs that produce proteins/peptides that share 90% identity with the amino acid sequence of the gene products of two, three or more of the L1R, A33R, A27L or B5R genes (or as described below, gene products of the monkeypox virus M1R, A35R, A29L or B6R gene).

In this invention, the term "ortholog" denotes the well-known meaning of this term. In this art, orthologs are genes in different species which evolved from a common ancestral gene. Due to their separation following a speciation event, orthologs may diverge, but usually have similarity at the sequence and structure levels; furthermore, orthologs usually have identical functions. Orthology is a type of homology. In this application, the term ortholog is used to include the ortholog gene (DNA or RNA) or the peptide/protein product of the ortholog. Sometimes the peptide/protein product of the ortholog is referred to as "ortholog product" or simply "ortholog". The meaning is evident from the context (e.g., a protein vaccine or immunogenic composition will contain peptides or proteins that may be referred to as orthologs—that is, products of an ortholog gene—of another poxvirus; a nucleic acid vaccine will contain nucleic acids that may be referred to as orthologs of another poxvirus—that is, an ortholog gene).

These vaccines and immunogenic compositions are based on recombinant vaccinia proteins or peptides that, when administered to a person or mammal, confer protection from poxviruses. (By "peptides" it is meant an amino acid sequence that is less than the full-length protein sequence.) The inventors have further discovered that a combination of recombinant vaccine modalities (nucleic acid plus proteins) was superior to either nucleic acid or proteins alone—for instance, a prime-boost regimen of a DNA vaccine prime followed by a protein vaccine conferred protection against severe monkeypox infection of rhesus macaques. Protection from disease correlated with the titers of binding antibodies to all proteins and to the extent of virus-specific $CD4^+$ T cell responses elicited by vaccination. (See data below.)

Thus, what is described here, in one embodiment, is a protein-based replacement vaccine and vaccination methodology to effectively protect against variola virus (smallpox), monkeypox virus, other poxviruses having 90% amino acid identity, and engineered poxviruses without any of the drawbacks associated with live-virus vaccines. This is especially relevant to immunocompromised persons who cannot be vaccinated with live vaccinia virus. It also represents an improvement over DNA vaccines alone, in terms of being simpler and more convenient, and often more effective.

One embodiment entails a protein vaccine against poxviruses. As shown in the details following, the inventors have demonstrated here the first reported protection in non-human primates, using the four proteins discussed below. However, to be effective, this vaccine comprises at least two purified recombinant monkeypox virus proteins or peptides—where at least one is specific to an IMV immunogen (ortholog product of L1R or A27L) and at least one is specific to an EEV immunogen (ortholog product of A33R or B5R). In the art, the monkeypox virus orthologs of L1R, A27L, A33R and B5R are designated, respectively, M1R, A29L, A35R and B6R. (It is noted that part of the description below designates the monkeypox orthologs as L1Ro, A27Lo, A33Ro and B5Ro, for simplicity.) For the vaccines, therefore, the at least two proteins or peptides are selected from the group consisting of a protein or peptide encoded by the open reading frame of the monkeypox ortholog genes M1R, A35R, A29L, and B6R, and natural or genetically engineered orthologs of these proteins or peptides having 90% identity (hereafter referred to sometimes as the monkeypox ortholog protein vaccine), where at least one least one peptide/protein is from the M1R or A29L genes or the respective ortholog products from other poxviruses which have 90% identity in the amino acid sequence, and at least one least one peptide/protein is from the A35R or B6R gene or the respective ortholog products from other poxviruses whose gene products have 90% identity in the amino acid sequence. The proteins may be the full-length proteins, or may only include the open reading frames. The proteins may include only the ectodomains, or the immunodominant B cell epitopes. Preferably, the vaccine includes three, and most preferably, all four of the proteins/peptides or their 90% identity ortholog products. The ortholog products having 90% identity are preferably derived from an orthopoxvirus selected from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof. The orthologs may be genetically engineered version of the monkeypox ortholog genes M1R, A35R, A29L, and B6R genes.

Due to the high homology between poxviruses, and the known data regarding the cross-protection by vaccines derived from them, this protein vaccine may be protective against poxviruses including orthopoxvirus such as camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof. The proteins of interest are those ortholog products that correspond to the products of the M1R, A35R, A29L, and/or B6R genes, which have 90% identity. If the corresponding virus has, for instance, only 50% homology with monkeypox virus, but the ortholog products of at least two of the gene products of M1R, A35R, A29L, and B6R have at least 90% identity in the amino acid sequence, then these ortholog products are useful as a vaccine for that virus. For instance, the camelpox virus has ortholog products that have at least 90% identity with the gene products of M1R, A35R, A29L, and B6R, and those ortholog products (two or more) will be useful as vaccine components of a vaccine against camelpox. Correspondingly, and very important to this invention, the monkeypox gene products of M1R, A35R, A29L, and B6R will also be useful as a vaccine against camelpox, and the camelpox ortholog products will be useful as a vaccine against monkeypox. The key is that the ortholog products have at least 90% identity to the gene products of M1R, A35R, A29L, and B6R. To that end, our invention in one embodiment contemplates a vaccine against poxviruses comprising at least two purified recombinant monkeypox virus proteins or peptides selected from the group consisting of (i) a protein or peptide encoded by the open reading frame of the monkeypox ortholog M1R gene, (ii) a protein or peptide encoded by the open reading frame of an ortholog of the monkeypox ortholog M1R gene, which protein or peptide has 90% amino acid sequence identity to a protein or peptide encoded by the open reading frame of an ortholog of the monkeypox ortholog M1R gene;

(iii) a protein or peptide encoded by the open reading frame of the monkeypox ortholog A29L gene, (iv) a protein or peptide encoded by the open reading frame of an ortholog of the monkeypox ortholog A29L gene, which protein or peptide has 90% amino acid sequence identity to a protein or peptide encoded by the open reading frame of an ortholog of the monkeypox ortholog A29L gene;

(v) a protein or peptide encoded by the open reading frame of the monkeypox ortholog A35R gene, (vi) a protein or peptide encoded by the open reading frame of an ortholog of the monkeypox ortholog A35R gene, which protein or peptide has 90% amino acid sequence identity to a protein or peptide encoded by the open reading frame of an ortholog of the monkeypox ortholog A35R gene;

(vii) a protein or peptide encoded by the open reading frame of the monkeypox ortholog B6R gene, and (viii) a protein or peptide encoded by the open reading frame of an ortholog of the monkeypox ortholog B6R gene, which protein or peptide has 90% amino acid sequence identity to a protein or peptide encoded by the open reading frame of an ortholog of the monkeypox ortholog B6R gene;

wherein at least one protein or peptide is (i), (ii), (iii) or (iv) and at least one protein or peptide is (v), (vi), (vii) or (viii), and an adjuvant.

Together with the protein vaccine, this invention contemplates other protein vaccines especially when used in conjunction with DNA vaccines. It is known that vaccination with DNA vaccines using vaccinia genes will achieve a response of cross-reaction and cross-protection against another poxvirus. Similar results were found regarding cross-reactivity using a DNA vaccine of monkeypox genes or a vaccine of monkeypox proteins, for instance in vaccinia plaque reduction neutralization tests and EEV spread inhibition assays. Since there is a high degree of cross-reactivity between vaccinia and monkeypox for all of the above-described four proteins/gene products, orthologs (especially from the variola virus which is extremely similar in sequence) having more than 90% identity will also cause immunogenic reactions in each other—and of course the orthologs will be best suited for causing immunogenic reactions in the respective poxvirus from which they are derived. Furthermore, it is preferred that the vaccines and immunogenic compositions described herein—whether DNA vaccine or protein vaccine/immunogenic composition—contain redundant IMV and EEV targets since this will increase cross-reactivity and cross-protection. Having such redundancy will provide enough or more than enough cross-reactive epitopes so as to afford vaccine protection—that is, because the proteins are so similar, the redundant nature of a DNA or protein vaccine containing three or four of the genes/gene products compensates for the possibility that the antibody to one protein won't cross-react with a particular virus. Hence, it is most preferred that the vaccines and immunogenic compositions contain all four of the genes/gene products L1R, A27L, A33R and B5R, or monkeypox orthologs, M1R, A29L, A35R and B6R, or other poxvirus orthologs/ortholog products.

The vaccines described herein, especially the protein vaccines, preferably include an adjuvant, such as CpG, alum, immune modulatory molecules, Toll-like receptor (TLR) stimulators and co-stimulatory markers. However, any known adjuvant that does not interfere with the efficacy or safety of the vaccine may be used.

As described below, the monkeypox ortholog genes M1R, A35R, A29L, and B6R are orthologs of VACV genes L1R, A33R, A27L and B5R, respectively. This disclosure also refers to the monkeypox ortholog genes M1R, A35R, A29L, and B6R as L1Ro, A33Ro, A27Lo and B5Ro, respectively, where the "o" indicates that the protein is an ortholog of the VACV protein.

Preferably, the purified recombinant monkeypox virus proteins or peptides are expressed from prokaryotic host cells such as E. coli, or synthesized in vitro, or expressed in mammalian cell lines.

In another embodiment, this invention entails an immunogenic composition that includes at least two purified recombinant monkeypox virus proteins or peptides encoded by the open reading frame of the monkeypox ortholog genes M1R, A35R, A29L, and B6R, and natural or genetically engineered orthologs of these proteins or peptides having 90% identity. At least one protein/peptide must be specific to an IMV immunogen (ortholog of L1R or A27L) and at least one must be specific to an EEV immunogen (ortholog of A33R or B5R). (As noted above the monkeypox virus orthologs of L1R, A27L, A33R and B5R are designated, respectively, M1R, A29L, A35R and B6R.) For the immunogenic compositions, therefore, the at least two proteins or peptides are selected from the group consisting of a protein or peptide encoded by the open reading frame of the monkeypox ortholog genes M1R, A35R, A29L, and B6R, and orthologs of these proteins or peptides having 90% identity (hereafter referred to sometimes as the monkeypox ortholog protein vaccine), where at least one least one peptide/protein is encoded by M1R or A29L, and at least one least one peptide/protein is encoded by A35R or B6R. The proteins may be the full-length proteins, or may only include the open reading frames. The protein may include only the ectodomains, or the immunodominant B cell epitopes. Preferably, the immunogenic composition includes three, and most preferably, all four of the proteins/peptides or their 90% identity orthologs. The orthologs having 90% identity are preferably derived from an orthopoxvirus selected from the group consisting of: camelpox virus, ectromelia virus, raccoon poxvirus, skunk poxvirus, Tatera poxvirus, Uasin Gishu virus, Volepox virus variola virus, vaccinia virus, monkeypox virus, gerbilpox and cowpox virus, or genetically engineered versions thereof. By "immunogenic composition", it is meant that this composition raises IMV neutralizing antibodies and raises antibodies that inhibit the spread of EEV or direct the destruction of infected cells. Immunogenic compositions may be useful for diagnostic kits, measuring antibody responses, and further research of poxviruses.

This invention also contemplates methods for inducing in a human or mammal an immune response against poxvirus infection (any of the poxviruses mentioned above, or any natural or genetically engineered poxvirus that has at least 90% identity in its amino acid sequence for any of the aforementioned genes, e.g., M1R, A35R, A29L and B6R) using the above-described monkeypox ortholog protein vaccines, administered to a subject in an immunologically effective amount, in a pharmaceutically acceptable carrier. One method of this invention utilizes this monkeypox protein vaccine alone, although it can be used together with other known poxvirus vaccines.

Another preferred embodiment entails a different method for vaccination against poxvirus infection, whereby a purified protein-based vaccine—such as but not limited to the above-described monkeypox ortholog protein vaccine described above—is used in conjunction with a nucleic acid-based vaccine that contains poxvirus nucleic acids, in a prime-boost regimen. Using this method of vaccination, the poxviruses protected against include, but are not limited to, orthopoxviruses such as camelpox virus, ectromelia virus, raccoon poxvirus, skunk poxvirus, Tatera poxvirus, Uasin Gishu virus, Volepox virus, variola virus, vaccinia virus, monkeypox virus, gerbilpox, and cowpox virus or genetically engineered versions thereof. Basically, any poxvirus having orthologs producing peptides/proteins having 90% identity to the amino acid sequences of the protein products of VACV genes L1R, A33R, A27L and B5R is a candidate for vaccine protection using these vaccines.

By "DNA vaccine", it is intended to include a gene-based or nucleic-acid vaccine with DNA or RNA encoding the proteins or peptides desired.

The present invention in all of its embodiments (e.g., nucleic acid vaccine or protein vaccine/immunogenic composition) includes VACV genes or their gene products or the ortholog genes and gene products found in the intracellular mature form of the virus (IMV) (for example, L1R and A27L genes and gene products, natural or genetically engineered) in combination with VACV genes or their gene products or ortholog genes and gene products found in the extracellular enveloped form of the virus (EEV) (for example, A33R and B5R genes and gene products, natural or genetically engineered). The vaccines should include at least one gene/gene product or ortholog gene/gene product from IMV and at least one from EEV, more preferably, the vaccines may consist of three or all four genes/gene products or ortholog genes/gene products.

Preferably, the recombinant poxvirus virus proteins or peptides contain B cell epitopes. As is described more below, the B cell epitopes have an advantageous role in protection. Preferably, the B cell epitope is located at amino acids 49-64 or 237-263 within the protein or peptide encoded by the open reading frame of the monkeypox ortholog B6R gene, amino acids 97-127 within the a protein or peptide encoded by the open reading frame of the monkeypox ortholog A35R gene, or amino acids 69-91 or 137-155 within the protein or peptide encoded by the open reading frame of the monkeypox ortholog M1R gene.

In this method the DNA vaccine is administered first as a prime vaccine and the purified protein vaccine is administered subsequently as a booster vaccine. For instance, such a vaccine protocol may comprise the steps of (a) administering to a human or other mammalian subject an immunologically effective amount of a DNA vaccine that includes at least three (but preferably four) of the following poxvirus nucleic acids: a nucleic acid encoding L1R, a nucleic acid encoding A33R, a nucleic acid encoding A27L, a nucleic acid encoding B5R, a nucleic acid encoding a ortholog of L1R, a nucleic acid encoding a ortholog of A33R, a nucleic acid encoding a ortholog of A27L, and a nucleic acid encoding a ortholog of B5R; and (b) subsequently administering to the subject an immunologically effective amount of the above-described monkeypox ortholog protein vaccine or a protein vaccine that includes at least two (but preferably three, and most preferably four) purified recombinant poxvirus virus proteins or peptides of the following: a protein or peptide encoded by the open reading frame of the L1R gene, a protein or peptide encoded by the open reading frame of the A33R gene, a protein or peptide encoded by the open reading frame of the A27L gene, a protein or peptide encoded by the open reading frame of the B5R, and orthologs (that is, products of the ortholog open reading frames) of these proteins or peptides having 90% identity, wherein at least one protein or peptide is encoded by the open reading frame of the L1R gene or A27L gene or the respective ortholog open reading frame of either, and at least one protein or peptide is encoded by the open reading frame of the A33R gene or B5R gene or the respective ortholog open reading frame of either; and an adjuvant. Also contemplated are genetically engineered variations of the orthologs and ortholog products, for instance, where the transmembrane region of a protein/peptide is removed, or the gene product is altered in any way as intended by the user.

With the DNA vaccine, it is preferred although not necessary that an adjuvant be included. Any adjuvant that does not inhibit the vaccine activity or safety would be acceptable, including those adjuvants described herein.

In a preferred embodiment, there is a second administration of the protein vaccine. Thus, the method may include the further step of (c) subsequently administering to said subject a second immunologically effective amount of a protein vaccine that includes at least two (but preferably three, and most preferably four) purified recombinant poxvirus virus proteins or peptides of the following: a protein or peptide encoded by the open reading frame of the L1R gene, a protein or peptide encoded by the open reading frame of the A33R gene, a protein or peptide encoded by the open reading frame of the A27L gene, a protein or peptide encoded by the open reading frame of the B5R, and orthologs (products of the ortholog open reading frames) of these proteins or peptides having 90% identity, wherein at least one protein or peptide is encoded by the open reading frame of the L1R or A27L gene or the respective ortholog open reading frame of either, and at least one protein or peptide is encoded by the open reading frame of the A33R or B5R gene or the respective ortholog open reading frame of either; and an adjuvant. Preferably, the orthologs may be obtained from the list of orthopoxviruses described above, including genetically engineered variations of these orthopoxviruses.

Such a DNA vaccine is described in U.S. Pat. No. 6,562,376. The DNA vaccine may be administered to the subject by intramuscular injection, intradermal injection, gene gun, electroporation, or biojector. The preferred modes of administration are by gene gun and electroporation. Preferably, the DNA vaccine comprises a nucleic acid encoding L1R or its ortholog, a nucleic acid encoding A33R or its ortholog, a nucleic acid encoding A27L or its ortholog, and a nucleic acid encoding B5R or its ortholog. In another preferred embodiment the DNA vaccine comprises at least three carrier particles, each carrier particle having a DNA sequence coated thereon, the DNA sequence comprising a promoter operative in the cells of a mammal and a protein coding region encoding for a poxvirus antigen chosen from the group consisting of: L1R antigen, A33R antigen, A27L antigen, B5R antigen, a ortholog of L1R antigen, a ortholog of A33R antigen, a ortholog of A27L antigen, and a ortholog of B5R antigen, wherein the at least three carrier particles each have a DNA sequence coated thereon having a protein coding region encoding for a different poxvirus antigens. Such a DNA vaccine composition, for administration by a gene gun or similar device, is described in U.S. Pat. No. 6,562,376.

The protein vaccine may be the monkeypox ortholog protein vaccine described, but this is not necessary for this vaccine regimen to be effective. Because of the known cross-protection between the various poxviruses, the purified protein products of the L1R, A33R, A27L and B5R genes from virtually any orthopoxvirus may be effective in this vaccine method. It is known that there are high levels of similarity between variola virus and other orthopoxviruses. Esposito et al., Science, Vol. 313, Aug. 11, 2006, pages 807-812. It is also known that vaccinia orthologs elicit protective immunity against monkeypox. In the field of poxviruses, orthologs have very high homology and functionality. Thus, orthologs of the protein products of the VACV L1R, A33R, A27L and B5R genes would be useful in the protein vaccine component of this method, especially orthologs having 90% identity with the protein products of these VACV genes. Such orthologs having 90% identity are preferably derived from an orthopoxvirus selected from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof. To that end, it is known that many of these orthopoxviruses share more than 90% identity in the orthologs of the four genes of interest (e.g., variola, monkeypox, vaccine, camelpox, mousepox (ectromelia)). For the purposes of this invention, if the corresponding virus has, for instance, only 50% homology with vaccinia virus, but the orthologs of at least two of the gene products of L1R, A33R, A27L and B5R have at least 90% identity in the amino acid sequence, then these orthologs are useful as a vaccine for that corresponding virus.

For instance, the variola virus has ortholog genes to the VACV genes L1R, A33R, A27L, and B5R. Further, the variola ortholog gene products have at least 90% identity with the gene products of L1R, A33R, A27L, and B5R. Those variola ortholog products (two or more) will be useful as vaccine components of a vaccine against variola. Correspondingly, and very important to this embodiment of the invention, the vaccinia gene products of L1R, A33R, A27L, and B5R genes will also be useful as a vaccine against variola, and the variola ortholog products will be useful as a vaccine against vaccinia. The key is that the ortholog products have at least 90% identity to the gene products of L1R, A33R, A27L, and B5R. It is noted here that the monkeypox ortholog genes M1R, A35R, A29L, and B6R produce peptides/proteins that also have at least 90% identity with the gene products of L1R, A33R, A27L, and B5R, and consequently would be useful as vaccine components in a vaccine against vaccinia or variola.

To that end, this invention contemplates in one preferred embodiment a method for inducing in a subject an immune response against poxvirus, comprising the steps of (a) administering to said subject an immunologically effective amount of a nucleic acid vaccine comprising at least three of the poxvirus nucleic acids selected from the group consisting of: a nucleic acid encoding L1R, a nucleic acid encoding A33R, a nucleic acid encoding A27L, a nucleic acid encoding B5R, a nucleic acid encoding an ortholog of L1R, a nucleic acid encoding an ortholog of A33R, a nucleic acid encoding an ortholog of A27L, and a nucleic acid encoding an ortholog of B5R; and (b) subsequently administering to said subject an immunologically effective amount of a protein vaccine comprising at least two purified recombinant poxvirus proteins or peptides selected from the group consisting of (i) a protein or peptide encoded by the open reading frame of the monkeypox ortholog B5R gene, (ii) a protein or peptide encoded by the open reading frame of an ortholog of the monkeypox ortholog B5R gene, which protein or peptide has 90% amino acid sequence identity to a protein or peptide encoded by the open reading frame of an ortholog of the monkeypox ortholog B5R gene;

(iii) a protein or peptide encoded by the open reading frame of the monkeypox ortholog A27L gene, (iv) a protein or peptide encoded by the open reading frame of an ortholog of the monkeypox ortholog A27L gene, which protein or peptide has 90% amino acid sequence identity to a protein or peptide encoded by the open reading frame of an ortholog of the monkeypox ortholog A27L gene;

(v) a protein or peptide encoded by the open reading frame of the monkeypox ortholog A33R gene, (vi) a protein or peptide encoded by the open reading frame of an ortholog of the monkeypox ortholog A33R gene, which protein or peptide has 90% amino acid sequence identity to a protein or peptide encoded by the open reading frame of an ortholog of the monkeypox ortholog A33R gene;

(vii) a protein or peptide encoded by the open reading frame of the monkeypox ortholog B5R gene, and (viii) a protein or peptide encoded by the open reading frame of an ortholog of the monkeypox ortholog B5R gene, which protein or peptide has 90% amino acid sequence identity to a protein or peptide encoded by the open reading frame of an ortholog of the monkeypox ortholog B5R gene;

wherein at least one protein or peptide is (i), (ii), (iii) or (iv) and at least one protein or peptide is (v), (vi), (vii) or (viii), and an adjuvant.

Additional administrations of a protein vaccine may be used, as many as deemed necessary depending on the subject's health, age, weight and life situation. For instance, the method may further include the step of subsequently administering to the subject an immunologically effective amount of a protein vaccine comprising at least two purified recombinant poxvirus proteins or peptides selected from the group consisting of (c) subsequently administering to said subject a second (or third, or more) immunologically effective amount of a protein vaccine comprising at least two purified recombinant poxvirus proteins or peptides selected from the group consisting of (i) a protein or peptide encoded by the open reading frame of the monkeypox ortholog B5R gene, (ii) a protein or peptide encoded by the open reading frame of an ortholog of the monkeypox ortholog B5R gene, which protein or peptide has 90% amino acid sequence identity to a protein or peptide encoded by the open reading frame of an ortholog of the monkeypox ortholog B5R gene;

(iii) a protein or peptide encoded by the open reading frame of the monkeypox ortholog A27L gene, (iv) a protein or peptide encoded by the open reading frame of an ortholog of the monkeypox ortholog A27L gene, which protein or peptide has 90% amino acid sequence identity to a protein or peptide encoded by the open reading frame of an ortholog of the monkeypox ortholog A27L gene;

(v) a protein or peptide encoded by the open reading frame of the monkeypox ortholog A33R gene, (vi) a protein or peptide encoded by the open reading frame of an ortholog of the monkeypox ortholog A33R gene, which protein or peptide has 90% amino acid sequence identity to a protein or peptide encoded by the open reading frame of an ortholog of the monkeypox ortholog A33R gene;

(vii) a protein or peptide encoded by the open reading frame of the monkeypox ortholog B5R gene, and (viii) a protein or peptide encoded by the open reading frame of an ortholog of the monkeypox ortholog B5R gene, which protein or peptide has 90% amino acid sequence identity to a protein or peptide encoded by the open reading frame of an ortholog of the monkeypox ortholog B5R gene;

wherein at least one protein or peptide is (i), (ii), (iii) or (iv) and at least one protein or peptide is (v), (vi), (vii) or (viii), and an adjuvant.

The protein vaccine may be administered to the subject by intramuscular injection, intradermal injection, and preferably by gene gun or electroporation. It is preferred that the protein vaccine is administered a minimum of a week following the administering of the DNA vaccine. It is generally contemplated that the protein vaccine will be preferably administered approximately two-three weeks after the DNA vaccine is administered, although the period between prime and boost vaccinations is well within the purview of someone skilled in this art to determine, and may vary with respect to the age, weight and health situation of the subject. For instance, for someone who is immunocompromised (such as an HIV-positive patient), it may be desirable to give a booster vaccination within one or two days following the DNA vaccine, followed up by additional boosters as rapidly and as many as is needed.

Furthermore, in the situation when someone is exposed to a poxvirus, such as smallpox, before receiving a vaccination, the protein vaccine DNA vaccine may be given, followed up within one, two or three days with the booster protein vaccine. Additional booster vaccines, preferably comprising the protein vaccine, may be desirable, and may also be given in one, two or three day intervals, until the desired immune response is achieved. This is known as a cluster dosing regimen.

Preferably, the protein vaccine comprises a protein or peptide encoded by the open reading frame of the L1R gene, a protein or peptide encoded by the open reading frame of the A33R gene, a protein or peptide encoded by the open reading frame of the A27L gene, and a protein or peptide encoded by the open reading frame of the B5R, and an adjuvant.

BRIEF DESCRIPTION OF THE FIGURES

FIG. 1B: Study design. Each DNA immunization consisted of four plasmids (4 mg each) given intramuscularly (3 mg) and intradermally (1 mg). Proteins (100 µg each) were either formulated in alum or mixed with 2 mg of CpG class B (TCGTCGTTTTGTCGTTTTCTCGTT) (SEQ ID NO:1) given by the intramuscular route. Challenge with monkeypox virus Zaire 79 ($5\times10^7$ pfu) was performed intravenously at the time (in weeks) indicated for each group.

FIG. 2A: ELISA antibody titers to monkeypox virus purified proteins. Sequential sera during the immunization regimen were tested to detect the presence of antibodies directed against the different monkeypox proteins (A27Lo, A33Ro, B5Ro, and L1Ro). Each data point on the y-axis represents the average of the response of all animals in each group. On the x-axis, the time of immunization is presented in weeks.

FIG. 2B: Antibody response to monkeypox proteins correlates cross-reactive response to homologous vaccinia proteins. The kinetic ELISA data in mOD/min for each protein and its ortholog are plotted against each other to demonstrate the significant antigenic cross-reactivity between the homologous proteins from the two distinct orthopoxviruses. Diamond=B5R/B5Ro. Open Triangle=A35R/A35Ro. Open Circle=L1R/L1Ro. Square=A27L/A27Lo.

FIG. 10: High-titer neutralizing antibody response against monkeypox virus and vaccinia virus after one DNA vaccination followed by 2 protein booster vaccinations. Serum collected on weeks 9, 14 and 33 were evaluated for MPOV and/or VACV neutralizing antibodies by plaque reduction neutralization test (PRNT). MPOV=monkeypox virus Z-79; VACV=vaccinia virus, strain IHD-J; PRNT50=plaque reduction neutralization test measuring lowest/highest dilution neutralizing 50% of the plaques; GMT=geometric mean titer. All assays were performed in duplicate, either within the same experiment or as an independent experiment.

FIG. 11: ELISA data (titers) showing responses against the four vaccine immunogens after a single DNA followed by a protein boost (see group 2, week 9). There are very high ELISA titers after the second protein boost (see group 2, week 14). B5Ro=ELISA using purified E. coli-expressed protein encoded by the monkeypox ortholog of the vaccinia B5R open reading frame. A33Ro=ELISA using purified E. coli-expressed protein encoded by the monkeypox ortholog of the vaccinia A33R open reading frame. L1Ro=ELISA using purified E. coli-expressed protein encoded by the monkeypox ortholog of the vaccinia L1R open reading frame. A27Lo=ELISA using purified E. coli-expressed protein encoded by the monkeypox ortholog of the vaccinia A27 open reading frame. ND=not done.

DETAILED DESCRIPTION OF THE PREFERRED EMBODIMENTS

Figure 1A:
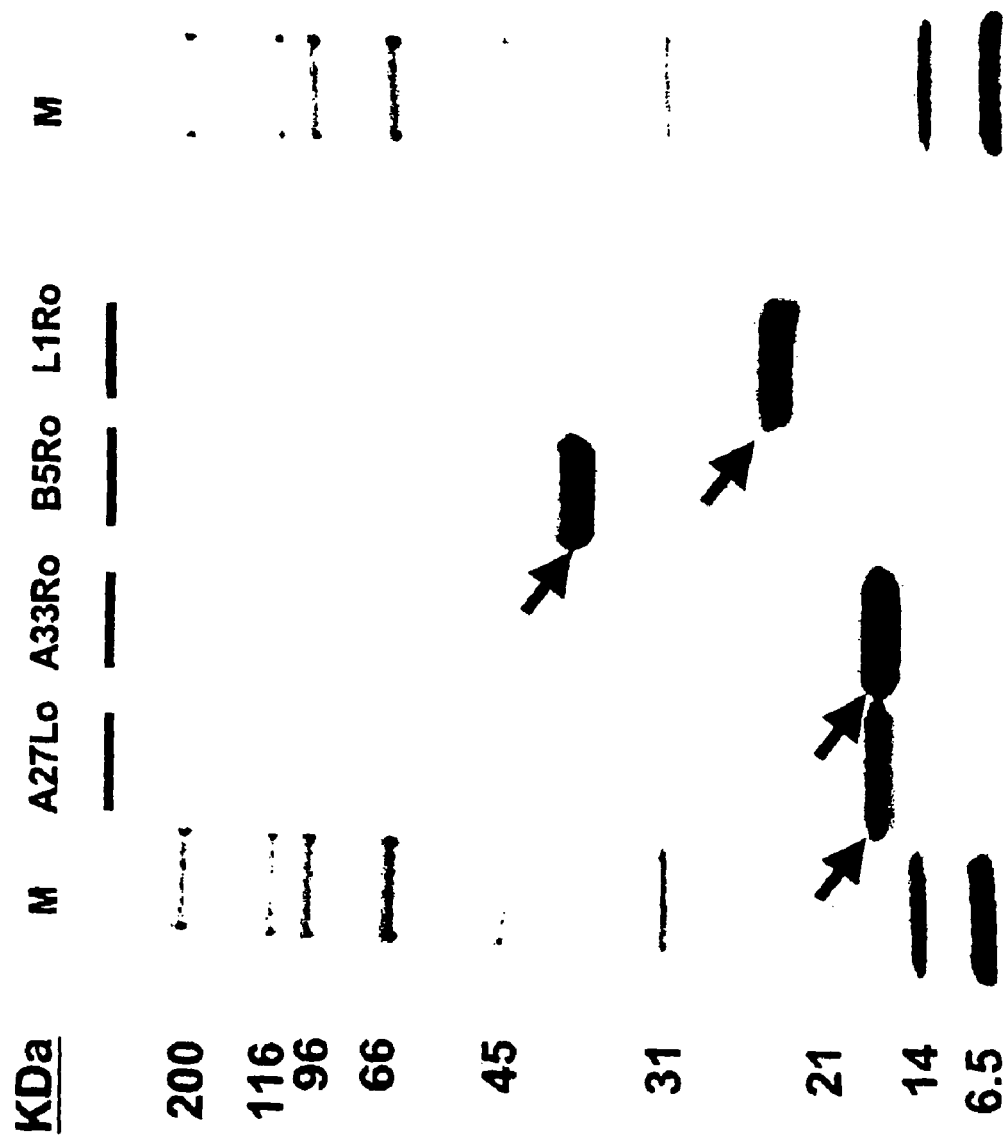
FIG. 1A: Bacterial expression of the VACV ortholog monkeypox proteins A27Lo, B5Ro, L1Ro, and A33Ro. Coomassie blue staining of recombinant proteins. The bacterial expression plasmids pETMPOX/A27Lo, pETMPOX/B5RoΔTM, pETMPOX/L1RoΔTM, and pETMPOX/A33RoΔTM were transformed into the expression host cells BL21(DE3). The monkeypox virus A27Lo protein was expressed as a soluble protein. Monkeypox B5Ro, L1Ro, and A33Ro proteins were expressed in inclusion bodies. After purification, protein expressions were confirmed by Western blot using VACV-immune sera.

In this paper is disclosed novel protein vaccines and methods of vaccination against poxviruses which contains monkeypox ortholog proteins or corresponding ortholog proteins of vaccinia or monkeypox. It is now possible to use such exogenously expressed proteins, or portions of proteins, to elicit immune responses that contribute to the protection against poxviruses in humans and other mammals. As described above, the novel protein vaccine includes at least two of the following purified recombinant monkeypox virus protein or peptide products produced by the monkeypox virus M1R, A35R, A29L and B6R open reading frames, and orthologs of these proteins or peptides having 90% amino acid identity, and an adjuvant. At least one of the peptides/proteins should be specific to an IMV immunogen (ortholog product of M1R or A29L) and at least one should be specific to an EEV immunogen (ortholog product of A35R or B6R). As noted above, preferably such orthologs are obtained from an orthopoxvirus such as those listed above, and may be naturally-occurring or genetically engineered. Basically, any poxvirus that has orthologs producing at least two peptides/proteins with 90% identity to the amino acid sequences of the protein products of VACV genes L1R, A33R, A27L and B5R (which includes the protein products produced by the monkeypox M1R, A35R, A29L and B6R genes) is a candidate for vaccine protection using these vaccines. Preferably the vaccine includes the four protein or peptide products produced by the monkeypox M1R, A35R, A29L and B6R open reading frames.

Any known adjuvant suitable for a vaccine can be used, as someone skilled in this art would know which adjuvant is appropriate. Examples of adjuvants include CpG, alum, immune modulatory molecules, TLR stimulators and co-stimulatory markers. CpG is a molecular (nucleic acid) adjuvant that acts on a certain Toll-like receptor. Immune modulatory molecules include those able to compensate for the absence of CD4± T cells, such as those implicated in HIV-infections.

In addition, the vaccines described herein can be combined with reagents which increase the antigenicity of the vaccine, or reduce its side effects. The decision to use such reagents is within the purview of someone skilled in this art.

These monkeypox ortholog protein vaccines are useful in methods for inducing an immune response against poxvirus infection. The vaccines may be administered to a subject human or mammal in an immunologically effective amount, along with a pharmaceutically acceptable carrier. Someone skilled in this art would be able to readily determine the appropriate dosage per each vaccinee, depending on the age, weight, and health situation of the vaccine. In addition, the choice of adjuvant influences the effectiveness of a dose. Standard dosage amounts and schedules for protein vaccines would apply for this invention as well. For example, a dosage amount might be between 50 micrograms and 1 milligram. Additional dosages may be needed or desired in individuals, as boosters.

This protein vaccine and method of vaccination has a number of advantages over the existing live virus vaccines. First, the vaccine is safer than live vaccinia virus vaccines. Further, the vaccine does not contain poxvirus immunomodulators contained in live poxvirus vaccines, which can decrease immune response. The vaccine is molecular and therefore more easily characterized and the mechanism of action more easily elucidated.

Also contemplated are immunogenic compositions including at least three purified recombinant monkeypox virus proteins or peptides encoded by the monkeypox virus M1R, A35R, A29L and B6R open reading frames, and orthologs of these proteins or peptides having 90% amino acid sequence identity.

Since the immune responses elicited by exogenously expressed proteins are almost exclusively targeted at B cell epitopes, rather than T cell epitopes, it is evident that the B cell epitopes on the proteins used in the vaccinations are important protective immunogens. It is believed that the B cell epitopes that are immunodominant contribute to protective immunity. Thus, the use of B cell epitopes expressed as proteins and administered as vaccinations, or at least booster vaccinations, is a way to reduce the ultimate number of vaccinations to achieve or maintain protective immunity. Since these are B cell epitopes, the antibody produced can be measured and protective immunity can be readily predicted. This is another advantage of this feature of the invention.

Thus, the protective basis of the protein-based poxvirus vaccines is antibody-mediated. Because target immunogens include those found on the surface of the infectious forms of virus (IMV and EEV) and on infected cells, it is possible that the protective antibodies function by neutralizing IMV and EEV, and by directing the destruction of infected by immune cells (e.g., natural killer cells) or by activated complement. Protective B cell epitopes are therefore identifiable, and a number of specific B cell epitopes are listed below. In addition, immunized macaques could also be a source of B cells from which to derive monoclonal antibodies that, once humanized, can be used for post-exposure treatment of individuals exposed to poxviruses, especially monkeypox and smallpox.

Thus, the recombinant monkeypox virus proteins or peptides preferably contain B cell epitopes, which may be immunodominant. Examples of B cell epitopes within the proteins include amino acids 49-64 or 237-263 within the protein or peptide encoded by the open reading frame of the monkeypox ortholog B6R gene, amino acids 97-127 within the a protein or peptide encoded by the open reading frame of the monkeypox ortholog A35R gene, and amino acids 69-91 or 137-155 within the protein or peptide encoded by the open reading frame of the monkeypox ortholog M1R gene.

The proteins of the monkeypox ortholog protein vaccine are preferably expressed in a prokaryotic expression system such as *E. coli*, or synthesized in vitro. *E. coli* is advantageous because it is generally easier to manufacture, and does not modify the protein produced.

Another important embodiment covers a vaccine regimen utilizing a poxvirus DNA vaccine as a first vaccine, and at least one subsequent poxvirus purified protein vaccine as follow-up booster vaccine(s). This vaccine protocol has unexpectedly been shown to be significantly more protective than either the DNA vaccine alone or the protein vaccine alone.

Gene-based vaccines to poxviruses are known which include combinations of immunogens to the IMV and EEV forms of poxviruses, as described in U.S. Pat. No. 6,562,376. The inventors found the immunogenicity of a gene-based poxvirus vaccine can be dramatically enhanced by boosting with a poxvirus purified protein vaccine. This invention is novel in the approach to poxvirus vaccines because it includes the combination of exogenously expressed proteins as vaccine components in addition to endogenously expressed proteins produced after gene-based vaccination. As one preferred example, the protein-based vaccine is useful to boost prior immunity primed by another vaccine, such as the DNA vaccine.

It has been demonstrated that a DNA vaccine comprised of the VACV A27L, A33R, B5R, and L1R genes (at least the open reading frames) administered by gene gun can confer protection from severe monkeypox (10); however, the vaccine-elicited immunity did not fully block viral replication in two of three animals and some pox lesions were still observed. The inventors tested the intramuscular route of DNA administration using the monkeypox ortholog genes. This route of DNA delivery was poorly immunogenic on its own; however, when the DNA prime was followed by a protein boost the inventors observed a higher antibody titer against monkeypox protein orthologs (A27Lo, A33Ro, B5Ro, and L1Ro), few lesions (<15), and better protection from disease. While the viral load in the plasma was under the limit of detection in group 1, the appearance of pox lesions indicated that viral dissemination was not completely halted by this immunization regimen. This may be explained either by the relatively high limits of detection or by the fact that the virus reservoirs were in internal organs rather than in the plasma.

Simple vaccines constituted of well-characterized DNA and proteins are amenable to manipulation with specific immune modulators to increase their immunogenicity and efficacy. In contrast, because live poxvirus vectors already express a plethora of cytokines and chemokines, the effects of immunomodulatory approaches may be difficult to dissect. Of note, neither the non-attenuated Dryvax nor the MVA or NYVAC protect immune-deficient animals (CD4$^+$ T cells<300) infected with SIV from lethal monkeypox, likely because of a defect in the maturation of high affinity protective antibodies in conditions of CD4$^+$ T cell depletion (13). The inventors have shown that simple subunit-based vaccines can be protective, and have shown how to manipulate the immune response of simple immunogens and generate a vaccine for smallpox that is safe and may confer protective immunity to people with congenital or acquired immune deficiency.

Figure 3C:
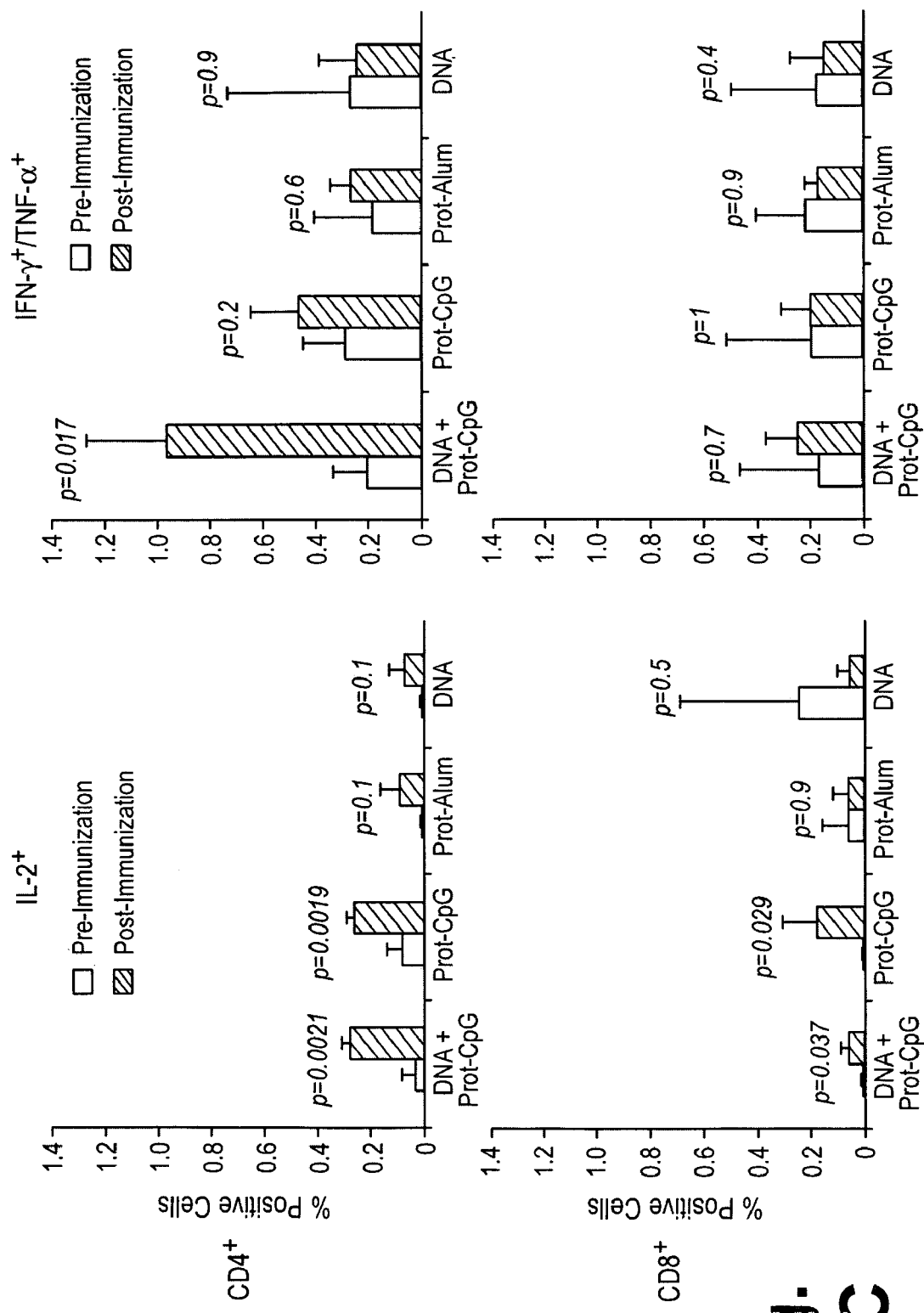
Figure 4:
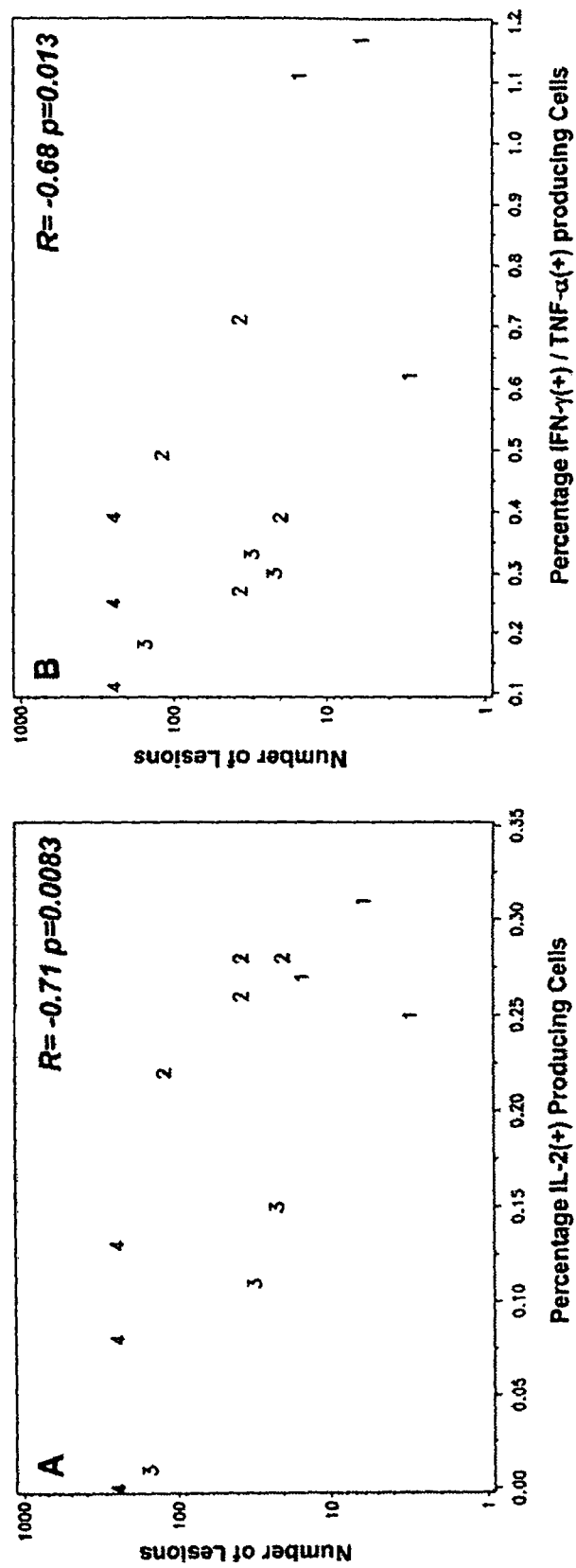
FIG. 4: Correlates of protection. Inverse correlation between maximum lesion number and monkeypox-specific $CD4^+$ T cells. Regression analysis of the percentage of $CD4^+$ T cell responses and the maximum number of lesions measured as $CD4^+$ T cells producing. IL-2 (A) or TNF-α and IFN-γ (B). Each number refers to data from animals of groups 1, 2, 3, and 4. Lesions too numerous to count were assigned the value 250 for plotting.

The inventors have demonstrated that a monkeypox-based subunit vaccine elicited sufficient antibody titers to protect against severe monkeypox and that monkeypox proteins can elicit antibodies that are cross-reactive with homologous vaccinia proteins. In addition, priming with DNA provided qualitative differences in the immune response by inducing a better CD4 helper response. Indeed it was observed that the group primed with DNA and immunized with protein (group 1) had a higher CD4 helper type 1 response (FIG. 3C) and, importantly, this response significantly correlated with a fewer number of lesions (FIG. 4). CD4 helpers are important but not sufficient, as we observed that groups that received only DNA showed the same response 2 weeks after the last DNA immunization (data not shown). These data are consistent with findings that $CD4^+$ T cell depletion following Dryvax vaccination was associated with a small number of pocks, whereas depletion of $CD8^+$ T cells was associated with complete protection (14). In mice, both $CD4^+$ T cells and antibodies have been shown to be important in protection from a VACV challenge (31), and, along the same line, CD4 or MHC class II knockout mice were poorly protected by MVA (32).

This invention highlights the importance of antibodies, as high neutralizing antibody titers of IMV correlated with a delay in the time of appearance of pox lesions and binding antibody titers inversely correlated with the lesion number. Our finding that macaque sera recognized epitopes within the B5R regions short consensus repeat 1 (20-72) and STALK (238-275), which are also recognized by monoclonal antibodies that neutralize EEV and inhibit 'comet' formation (16, 26), underscores the importance of these epitopes in halting virus spread in the host. Indeed, the sera of these animals had inhibitory activity in a novel EEV spread inhibition assay (Table II). Recent studies using passive immunization of mice with chimpanzee/human anti-B5R monoclonal antibody showed a protection of mice intranasally challenged with virulent VACV. The protective monoclonal antibodies bound to an epitope that maps within the same amino acid stretch of B5R recognized by the sera from our protected animals (33).

TABLE II

Humoral immune response elicited by vaccination[a]

| Macaque | Treatment | Neutralizing Ab Titer to Vaccinia (IMV) β-Gal assay Prevaccine | Neutralizing Ab Titer to Vaccinia (IMV) β-Gal assay Prechallenge | Neutralizing Ab Titer to Vaccinia (IMV) Plaque reduction assay Prechallenge | Neutralizing Ab Titer to Monkeypox (IMV) Plaque reduction assay Prechallenge | Neutralizing Ab Titer to Monkeypox (EEV) Spread reduction assay Prevaccine | Neutralizing Ab Titer to Monkeypox (EEV) Spread reduction assay Prechallenge |
|---|---|---|---|---|---|---|---|
| Group 1 | DNA + proteins-CpG | | | | | | |
| 482 | | <20 | 1:214 | 80 | 202 | <25 | 100 |
| 489 | | <20 | 1:237 | ≧640 | 640 | <25 | 100 |
| 496 | | <20 | 1:304 | 160 | 202 | <25 | 50 |
| Group 2 | Proteins-CpG | | | | | | |
| 498 | | <20 | 1:294 | 160 | 80 | <25 | <25 |
| 499 | | <20 | 1:325 | 80 | 80 | <25 | <25 |
| 500 | | <20 | 1:121 | 80 | 160 | nd | 25 |
| 501 | | <20 | 1:506 | 320 | 1280 | nd | <25 |
| Group 3 | Proteins + Alum | | | | | | |
| 480 | | <20 | 1:1780 | 160 | 320 | <25 | 25 |
| 481 | | <20 | 1:744 | 320 | 453 | nd | 50 |
| 497 | | <20 | 1:421 | ≧640 | 1280 | nd | 100 |
| Group 4 | DNA | | | | | | |
| 479 | | <20 | 1:76 | <20 | <20 | nd | <25 |
| 488 | | <20 | 1:97 | <20 | 28 | nd | <25 |
| 491 | | <20 | 1:93 | <20 | <20 | nd | <25 |

[a]Sera from all animals were collected before immunization and 1 wk before challenge exposure to monkeypox virus. In the neutralization assay for VACV IMV with the β-Gal assay, each sample was tested in four replicates at four consecutive dilutions in two independent assays. In the monkeypox IMV plaque reduction assay, the values represent the geometric mean titers (50% neutralization) of two independent experiments. The monkeypox EEV spread inhibition assay titers represent the reciprocal of the highest serum dilution inhibiting the formation of satellite plaque numbers by at least 60% (titers represent results obtained from one assay). Prebleed sera for 482, 489, 496, 498, 499, and 480 were tested, and all exhibited titers <25 (data not shown). nd = not done.

Antibody-dependent cell (or activated complement) cytotoxicity also may be involved in protection. Indeed, in one study, individuals vaccinated 15 to 18 years before the time of testing showed residual immunity only in an antibody-dependent cell cytotoxicity assay (34).

In its essential format, this novel vaccination method induces in a human or mammalian subject an immune response against poxvirus, using at least two steps. The first step is administering to a vaccinee an immunologically effective amount of a DNA vaccine. The DNA vaccine must contain at least three of the poxvirus nucleic acids selected from the group consisting of: a nucleic acid encoding L1R, a nucleic acid encoding A33R, a nucleic acid encoding A27L, a nucleic acid encoding B5R, a nucleic acid encoding a ortholog of L1R, a nucleic acid encoding a ortholog of A33R, a nucleic acid encoding a ortholog of A27L, and a nucleic acid encoding a ortholog of B5R. The ortholog protein products should have at least 90% identity to the products of the VACV genes L1R, A33R, A27L and B5R. Sources of the orthologs are preferably within the orthopoxvirus family, such as camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof.

The second step is subsequently administering to the vaccinee an immunologically effective amount of a protein vaccine comprising at least two (and preferably three or four) purified recombinant poxvirus virus proteins or peptides selected from the group consisting of a protein or peptide encoded by the open reading frame of the L1R gene, a protein or peptide encoded by the open reading frame of the A33R gene, a protein or peptide encoded by the open reading frame of the A27L gene, a protein or peptide encoded by the open reading frame of the B5R, and orthologs of these proteins or peptides having 90% amino acid identity, where at least one protein or peptide is produced from the L1R or A27L gene or produced from an ortholog of either, and at least one is produced from the A33R or B5R gene or produced from an ortholog of either; and an adjuvant such as those described above.

Additional booster vaccinations may be given, usually comprising another dose of the protein vaccine, or a variation of the protein vaccine, perhaps including a different combination of purified proteins or peptides selected from the list.

The source of the ortholog proteins may be any poxvirus, since, as described above, cross-protection among the poxviruses—especially among smallpox, monkeypox and vaccinia—is known. What is generally required in order for a vaccine to be effective against a poxvirus is that the protein components have at least 90% identity in amino acid sequence to the protein products of the vaccinia genes L1R, A33R, A27L or B5R (which would include, of course, orthologs such as the monkeypox orthologs, and orthologs from other orthopoxvirus such as camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof). Thus, as an example, ortholog proteins from ectromelia virus having 90% identity to vaccinia genes L1R, A33R, A27L or B5R may be useful as vaccine components in a vaccine against raccoon poxvirus, as long as the raccoon poxvirus itself has ortholog proteins having 90% identity to vaccinia genes L1R, A33R, A27L or B5R. Of course, it is most preferred that a vaccine against raccoon poxvirus contain the ortholog proteins derived from the raccoon poxvirus; however, this is not always convenient or even necessary for the vaccine to be effective as long as the other criteria are met.

The protein vaccine may be administered by any known method, such as by intramuscular injection, intradermal injection, gene gun or electroporation. Preferably, the protein vaccine is administered a minimum of a week following the administering of the DNA vaccine. It is contemplated that the protein vaccine booster would be administered approximately two-three weeks following the prime DNA vaccine vaccination. However, someone skilled in this art would readily be able to determine the appropriate schedule for administering the protein vaccine booster (e.g., evidence of immune response or lack thereof following initial administration).

Someone skilled in this art would be able to readily determine the appropriate dosage per each vaccinee, depending on the age, weight, and health situation of the vaccine. In addition, the choice of adjuvant influences the effectiveness of a dose. Standard dosage amounts and schedules for protein vaccines would apply for this embodiment of the invention as well. For example, a dosage amount might be between 50 micrograms and 1 milligram. Additional dosages may be needed or desired in individuals, as further boosters.

The DNA vaccine (or gene-based vaccine to include RNA encoding the proteins or peptides described above) may be administered by any known methods, including by intramuscular injection, intradermal injection, electroporation, biojector, by oral or pulmonary delivery, inoculation by particle bombardment (i.e., 15, gene gun), or by viral vector (e.g., alphavirus replicon, adenovirus-vectored vaccine). Any of these methods can be used to deliver gees as long as the nucleic acid is expressed and the desired antigen is made in the cell. DNA (or gene-based) vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

The dosage of the DNA vaccine depends on how it is administered (e.g., gene gun or electroporation or other mode), and can be determined readily by someone having skill in this art. For instance, a dosage may be 300 micrograms or more, although this is just an example.

The nucleic acid encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 Molecular Cloning: A Laboratory Manual or DNA Cloning, Vol. I and II (D. N. Glover, ed., 1985) for general cloning methods. Suitable plasmids are described in U.S. Pat. No. 6,562,376.

One preferred DNA vaccine comprises all four of a nucleic acid encoding L1R or its ortholog, a nucleic acid encoding A33R or its ortholog, a nucleic acid encoding A27L or its ortholog, and a nucleic acid encoding B5R or its ortholog.

One preferred protein vaccine comprises all four of a protein or peptide encoded by the open reading frame of the L1R gene, a protein or peptide encoded by the open reading frame of the A33R gene, a protein or peptide encoded by the open reading frame of the A27L gene, and a protein or peptide encoded by the open reading frame of the B5R.

The prime-boost vaccine regimen may be administered according to standard schedules of vaccination, and the best course would be readily determined by someone skilled in this art depending on the particular vaccine's needs, even on a case by case basis if necessary. In general, the protein vaccine should be administered a minimum of a week following the administering of the DNA vaccine, and preferably administered approximately two-three weeks after the DNA vaccine. However, the period between prime and boost vaccinations may vary with respect to the age, weight and health situation of the subject. For instance, an immunocompromised patient (such as an HIV-positive patient) or children or others with excema, may need an unconventional dosage and vaccination schedule, where booster vaccinations are multiple and within one or two days of each other.

In the situation when someone is exposed to a poxvirus, such as smallpox, before receiving any sort of poxvirus vaccination, a cluster dosing regimen may be desirable, where the prime DNA vaccine is followed in quick succession (1-3 day intervals) with multiple boosters of the protein vaccine.

In the situation where someone is exposed to a poxvirus, such as smallpox, and has received a previous poxvirus vaccination (i.e. Dryvax or even the instant DNA or protein vaccines), a single protein vaccination could rapidly boost the antibody responses to protective B cell epitopes. This type of vaccine would not be affected by pre-existing neutralizing antibody, whereas the use of Dryvax might not be effective because the vaccinia virus in that vaccine might be unable to elicit further or adequate immunogenic reaction due to the pre-existing anti-vaccinia antibody. For a more extended regimen, one dose of the DNA vaccine, followed by weekly boosters for as long as needed, may be adequate.

One preferred vaccination method that has shown good results is the combination of a first vaccination with the above-described DNA vaccine, and two subsequent booster vaccinations with the purified protein vaccine. Monkeys were vaccinated via electroporation with one dose of a DNA vaccine containing four monkeypox nucleic acids: a nucleic acid encoding M1R, a nucleic acid encoding A35R, a nucleic acid encoding A29L, a nucleic acid encoding B6R. Subsequently, the monkeys received a booster vaccination with the monkeypox ortholog protein vaccine containing four purified recombinant monkeypox virus proteins encoded by the open reading frame of the monkeypox ortholog genes M1R, A35R, A29L, and B6R. Following this, the monkeys were given a second monkeypox ortholog protein vaccine using the same vaccine as the first booster. Upon testing, the monkeys had surprisingly high antibody responses. See FIGS. 9, 10, 11 and 12.

As with all of the vaccines and methods of vaccination described herein, effectiveness is achieved only if the severity of the disease symptoms are reduced. It is preferred that these immunization methods be at least 20% effective in preventing death in an immunized population after challenge with poxvirus. More preferably, the vaccination method is 50% or more effective, and most preferably 70-100% effective, in preventing death in an immunized population. The vaccination method is shown herein to be 100% effective in the mouse and non-human primate models for poxvirus. In contrast, unimmunized animals are uniformly killed by challenge with poxvirus. Our results indicate that vaccination with our vaccines and methods of vaccination provides protection against a lethal poxvirus infection.

The various embodiments of this invention lend themselves to multiple applications. For instance, both the monkeypox ortholog protein vaccine and the DNA vaccine—protein vaccine method of vaccination can be (1) replacements for the existing smallpox vaccine;
(2) alternative vaccines on a case-by-case basis, such as for instance, for persons excluded from live-virus vaccination;
(3) followed by a classical smallpox vaccine boost to reduce adverse events;
(4) a focused booster vaccination in persons previously vaccinated with the classical smallpox vaccine;
(5) a booster vaccination in persons previously vaccinated with a molecular smallpox vaccine;
(6) a "picket" vaccine to provide some level of protection against a smallpox attack—a classical smallpox vaccine booster vaccination would be administered if an attack occurred or was imminent.

Other categories of persons for whom these vaccines and methods of vaccination might be useful include persons working in the biotech field who are exposed to poxviruses, and who must make sure have up-to-date boosts; and first responder medical personnel.

The present invention also provides kits which help facilitate using the present vaccines and methods. The kits comprise a first container containing the above-described monkeypox ortholog protein vaccine, or another embodiment of the protein vaccine. The kits also may include DNA for the DNA vaccine, frozen or lyophilized, in a second container. With the second container, there is also included a container for a coating solution or the premixed, premeasured dry components of the coating solution, and another container which contains the small, inert, dense particles in dry powder form or suspended in 100% ethanol. These container means can be made of glass, plastic or foil and can be a vial, bottle, pouch, tube, bag, etc. The kit may also contain written information, such as procedures for carrying out the present invention or analytical information, such as the amount of reagent (e.g. moles or mass of DNA) contained within the kit. The written information may be on any of the various containers, and/or a separate sheet included.

Other features of the invention will become apparent in the course of the following descriptions of exemplary embodiments which are given for illustration of the invention and are not intended to be limiting thereof.

As described below, the inventors immunized rhesus macaques with plasmid DNA encoding the monkeypox orthologs of the VACV L1R, A27L, A33R, and B5R proteins by the intradermal and intramuscular routes, either alone or in combination with the equivalent recombinant proteins produced in E. coli. Animals that received only DNA failed to produce high titer antibodies, developed innumerable skin lesions after challenge, and died in a manner similar to placebo controls. By contrast, the animals vaccinated with proteins developed moderate to severe disease (20-155 skin lesions) but survived. Importantly, those immunized with DNA and boosted with proteins had mild disease with fifteen or fewer lesions that resolved within days. DNA/protein immunization elicited T helper responses and binding antibody titers to all four proteins that correlated negatively with the total lesion number. The sera of the immunized macaques recognized a limited number of linear B cell epitopes that are highly conserved among orthopoxviruses.

Animals, Immunization, and Monkeypox Virus Challenge.

Fourteen colony-bred rhesus macaques (*Macaca mulatta*), obtained from Covance Research Products (Alice, Tex.), were housed and handled in accordance with the standards of the American Association for the Accreditation of Laboratory Animal Care. The study was reviewed and approved by the animal care and use committees at Advanced BioScience Laboratories (Kensington, Md.) and Southern Research Institute (Frederick, Md.). Each DNA immunization consisted of four plasmids (4 mg each) given intramuscularly (3 mg) and intradermally (1 mg) at different locations. Proteins (100 µg each) were either formulated in alum (Rehydragel HPA, Reheis, Berkeley Heights, N.J.) or mixed with 2 mg of CpG-B ODN 2006 (TCGTCGTTTTGTCGTTTTGTCGTT) (SEQ ID NO:2) (Coley Pharmaceutical Group, Wellesley, Mass.) given by the intramuscular route. Monkeypox virus (Zaire 79 strain) was administered by the intravenous route 5 weeks after the last protein boost (week 35 from the beginning of immunization) at a dose of $5 \times 10^7$ pfu to animals from groups 1, 4, and 5. Macaques in groups 2 and 3 were challenged at week 41 with the same dose of the same viral stock. Following challenge, animals were monitored daily for activity, the appearance of skin lesions, and development of lesions through the stages of papule, vesicle, pustule, and scab.

Real-Time PCR to Detect Monkeypox Virus Genomes.

DNA was extracted from frozen blood samples using the QIAamp DNA mini kit (Qiagen, Valencia, Calif.) (20). The primers OPHA-F89 (5'-GATGATGCAACTCTATCATGTA-3') (SEQ ID NO:3) and OPHA-R219 (5'-GTATAATTAT-CAAAATACAAGACGTC-3') (SEQ ID NO:4) and the probe OPHA-p143S-MGB (5'-FAMAGTGCTTGGTATAAG-GAGMGBNFQ-3') (SEQ ID NO:5) were selected from the hemagglutinin gene (GenBank # L22579; ORF J7R). While the primers were synthesized by Invitrogen (Carlsbad, Calif.), the TaqMan probe was synthesized by PE Biosystems (Foster City, Calif.) and it contained 6-carboxyfluorescein (FAM) in the 5' end and the NFQ and the MGB in the 3' end.

The 5' nuclease PCR reaction and amplification conditions were performed using Platinum Taq DNA polymerase (Invitrogen). All reactions included at least one positive control that had one hundred copies of cloned target DNA and one no-template control. The positive control for each run established the threshold Ct value for positivity. Samples yielding Ct values that marginally exceeded the threshold value were retested. If the Ct value was confirmed as exceeding the threshold after retesting, the sample was considered negative (contained less than 5,000 copies).

Measurement of VACV Neutralizing Antibodies.

Sera from monkeys were collected 3 weeks after the last protein immunization (1 week before challenge), heat-inactivated (56° C. for 30 min), and evaluated for the presence of VACV neutralizing antibodies using a novel assay based on expression of a reporter gene, β-galactosidase (β-Gal) (21).

Briefly, a recombinant VACV vSC56, expressing β-Gal under the control of a synthetic early/late promoter (22), was used to develop a neutralization assay based on a single-round infection of HeLa cells (CCL-2, American Type Culture Collection, Manassas, Va.). This is a rapid (24 h), high throughput assay that was shown to have similar sensitivity to the classical plaque reduction neutralization tests. Each assay includes as a positive control FDA Standard Reference Vaccinia Immunoglobulin (VIG) obtained from Dynport vaccine company (Frederick, Md.) and validated at the Center for Biologics Evaluation and Research (FDA). Negative controls included plasma from unvaccinated children and albumin. Four serial dilutions of each monkey plasma were pre-incubated with vSC56 virus for 60 min at 37° C. and then dispensed into ninety-six-well round bottom plates containing $1\times10^5$ HeLa cells per well (five replicates per antibody dilution). Plates were incubated for an additional 16 h at 37° C. in a humidified $CO_2$ incubator. Cells were then lysed with the detergent IGEPAL CA630 (Sigma, St. Louis, Mo.). In the second stage of the assay, β-Gal enzymatic activity in each well was measured using ninety-six-well Immunlon 2 plates (Thermo Labsystems, Franklin, Mass.). Each plate included a β-Gal standard curve using a recombinant 13-Gal enzyme (Roche Diagnostics Corporation, Indianapolis, Ind.). Chlorophenol red beta-D-galactopyranoside monosodium salt (CPRG) substrate (Roche Diagnostics) was added to all wells for 30 min at room temperature in the dark, and the enzymatic reaction was stopped with 1M $Na_2CO_3$ solution. Optical density (OD) was determined at 575 nm by an ELISA reader. OD readings were transferred to Microsoft Excel for further analysis. The 13-Gal standard curves were used to convert OD values into β-Gal activity per experimental or control group (in mU/ml). The β-Gal activity of each experimental group (virus mixed with a given dilution of test plasma) was expressed as percentage β-Gal activity in the virus-only control wells. Microsoft Excel was used to plot the percentage of control values for the serial dilutions of each plasma versus log dilutions. The equation of each curve was used to calculate the 50% inhibitory dilution ($ID_{50}$).

The plaque reduction assays were performed essentially as described previously (17); however, BSC-1 cells and a semi-solid overlay were used. Briefly, VACV strain IHD-J or monkeypox virus Zaire 79 was diluted in complete medium (Earle's minimal essential medium containing 5% heat-inactivated FBS, antibiotics [100 U/ml penicillin, 100 μg/ml of streptomycin, and 50 μg/ml of gentamicin], and 10 mM HEPES) to give ~500 pfu/ml. Aliquots of this viral suspension (100 μl) were incubated with an equal volume of serum diluted in complete medium (serum samples were heat activated, 56° C. for 30 min, before dilution) for 1 h at 37° C. and then 180 μl of sample was adsorbed to confluent BSC-1 cell monolayers in six-well plates for 1 h in a 37° C. 5% $CO_2$ incubator. A 2 ml semisolid overlay (Earle's basal minimal essential medium, 1.5% methyl cellulose, 5% heat-inactivated FBS, antibiotics) was added to each well. Plates were incubated in a 37° C. 5% $CO_2$ incubator for 4 days for VACV or 6 days for monkeypox virus: Cell monolayers were stained with 1 ml of crystal violet staining solution (2% crystal violet, 70% ethanol). Plaques were counted and the percent neutralization was calculated relative to the number of plaques in the absence of antibody. Titers represent the reciprocal of the highest dilution resulting in a 50% reduction in the number of plaques.

EEV Spread Inhibition Assay.

This assay is similar to a comet inhibition assay; however, a semisolid overlay is added after monkeypox virus EEV have been released from initially infected cells; the resulting satellite plaques are given a few days to enlarge and are then counted. Specifically, 200 μl of complete media containing 20-30 pfu of monkeypox virus was adsorbed to monolayers of BSC-1 cells in six-well plates for 1 h in a 37° C. 5% $CO_2$ incubator. Unbound virus was removed by rinsing once with 2 ml of complete medium. Monkey serum serial-diluted in 1.5 ml of complete medium was then added to duplicate wells. A no-inhibition control plate was overlaid with complete medium containing no serum, and a no-spread control plate was overlaid with semisolid overlay. The plates were incubated in a 37° C. 5% $CO_2$ incubator for 48 h to allow EEV to release from infected cells. The liquid overlay was then removed and 2 ml of semisolid overlay was added to each well to prevent additional EEV spread. After an additional 2 days (5 days after virus adsorption) the monolayers were stained with 1 ml of crystal violet staining solution. Plaques were then counted. EEV spread was determined by subtracting the average number of plaques in the no-spread control wells from the number of plaques in the no-inhibition control wells. EEV spread inhibition titers represent the reciprocal of the highest serum dilution that inhibited EEV spread by 60%.

Plasmid Production and Bacterial Expression.

The monkeypox orthologs of the VACV A27L, A33R, B5R, and L1R genes are A29L, A35R, B6R, and M1R, respectively. In this manuscript we will refer to the protein products of the monkeypox A29L, A35R, B6R, and M1R open reading frames as A27Lo, A33Ro, B5Ro, and L1Ro, respectively, where the 'o' is included to indicate that the protein is an ortholog of the VACV Copenhagen protein. The VACV designations are retained to simplify referrals to earlier work involving the VACV orthologous proteins.

DNA vaccine plasmids containing the monkeypox A29L, A35R, B6R, and M1R genes pMPOX/A27Lo (where the 'o' refers to ortholog), pMPOX/A33Ro, pMPOX/B5Ro, and pMPOX/L1Ro, respectively, have been described previously (23).

The monkeypox genes were subcloned from the aforementioned DNA vaccine plasmids into prokaryotic expression vectors to produce recombinant proteins from *E. coli*. The monkeypox gene A29L (GenBank # AY160186) was PCR-amplified from DNA plasmid pMPOX/A27Lo utilizing Hot Star Taq Polymerase (Qiagen) and PCR primers made by Invitrogen (5'GATATACATATGGACGGAAACTCTTTTC-CCCGGAGAT-3', 5'CTCGAGTGCGGCCGCCTCATAGG-GACGCCGTCCAGTCTGTACAT-3') (SEQ ID NOS:6 and 7, respectively). The gene was digested with the restriction enzymes Nde1 and Not1 and directionally cloned into the expression vector pET26b (Novagen, San Diego, Calif.), which contains a six-HIS tag on the C terminus. The monkeypox genes A33Ro (GenBank # AY160188), B5Ro (GenBank # AY160189), and L1Ro (GenBank # AY160187) were constructed in a similar method with the exception that these proteins were cloned to express only their extracellular domains to increase protein expression and facilitate purification without compromising the immunogenic determinants of the extracellular domain. The monkeypox A33RoΔTM gene was amplified from N(60)-T(181) utilizing the primers 5'-GATATACATATGAATCAATGCATGTCTGCTAACG-3' (SEQ ID NO:8) and 5'-CTCGAGTGCGGCCGCTGTA-CAAAAATACTTTCTAACTTCTTGTGATACAT3' (SEQ ID NO:9). The monkeypox B5RoΔTM gene was amplified from M(1)-H(279) utilizing the primers 5'-GAGATATATA-CATATGAAAACGATTTCCGTTGTTACGTTGTTATG-3' (SEQ ID NO:10) and 5'GCTCGAGTGCGGCCGCAT-GATAAGTTGCTTCTAACGATTCT-3' (SEQ ID NO:11). The monkeypox L1RoΔTM gene was amplified from A(3)-Q(185) utilizing the primers 5'-GAGATATACATATG-GCAGCAAGCATACAGACGACTGTGAA-3' (SEQ ID NO:12) and 5'-GTCGAGTGCGGCCGCAAACTGAACTC-CTGTACCAGCAACTT-3' (SEQ ID NO:13). The extracellular domains were determined utilizing the software TM Predict, which is commonly used for prediction transmembrane regions and their orientation. The algorithm is based on the statistical analysis of TMbase, a known database of naturally occurring transmembrane proteins. The prediction is made using a combination of several weight-matrices for scoring. (K. Hoffmann & W. Stoffel, (1993) TMbase—A database of membrane spanning proteins segments, Biol. Chem. Hoppe-Seyler 374,166) The program was also used for comparison of structural similarities to VACV proteins. Plasmid constructs were confirmed by enzyme restriction digestion and by PCR.

The bacterial expression plasmids pETMPOX/A27Lo, pETMPOX/B5RoΔTM, pETMPOX/L1RoΔTM, and pETMPOX/A33RoΔTM were transformed into the expression host cells BL21(DE3) (Novagen). Cells were grown in LB-Kan (50 μg/ml) at 37° C. to a cell density of OD600=0.6-1. Cells were induced with 1 mM IPTG for 2 h at 37° C. The recombinant monkeypox proteins were named using the nomenclature for the equivalent VACV proteins. The monkeypox A27o protein was expressed as a soluble protein. The monkeypox A33Ro, B5Ro, and L1Ro proteins were expressed in inclusion bodies. The cells were harvested by centrifugation at 5,000×g for 15 min and stored at −70° C. until purification.

Protein Purification.

The bacterial cell pellet for monkeypox A27Lo was chemically lysed with Buffer A (50 mM Tris-HCL pH7.5, 300 mM NaCl, 10% sucrose, 10 mM imidazole, 0.1% Triton X-100, 1× protease inhibitors, and 50 μg/ml lysozyme). The cells were resuspended in Buffer A and incubated at 21° C. for 15 min with gentle rocking.

Viscosity of the lysate was reduced by the addition of Benzonase (Novagen) at 1 U/μl with further incubation at 21° C. for 10 min. The cell lysate was centrifuged at 16,000×g for 45 min to remove the insoluble material. The protein was then bound on the immobilized metal affinity chromatography HIS Select (Sigma). The protein was eluted with 50 mM and 250 mM imidazole in Buffer B (50 mM Tris pH 7.5, 150 mM NaCl, 10% glycerol). Imidazole was removed from the protein using a PD10 desalting column (Amersham, Piscataway, N.J.) and collected with Buffer B. Proteins A33Ro, B5Ro, and LIRo were expressed and purified from inclusion bodies utilizing the Protein Refolding Kit (Novagen). The cell pellets were chemically lysed similar to monkeypox A27Lo without the addition of imidazole. The inclusion bodies were homogenized, washed three times with wash buffer (20 mM Tris-HCl, pH 7.5, 10 mM EDTA, 1% Triton X-100), and resuspended in solubilization buffer (50 mM CAPS, 0.3% N-Lauroylsarcosine, and 0.1 mM DTT, pH 11) for 15 min at 21° C. The supernatant was clarified by centrifugation at 10,000×g for 10 min. Protein refolding was accomplished through dialysis against 20 mM Tris pH 8.5 and 0.1M DTT. Residual detergent was removed from the proteins by anionic exchange on a Dowex column (Bio-Rad, Hercules, Calif.). Subsequently, the proteins were bound to the immobilized metal affinity chromatography, HIS Select (Sigma) and were eluted with 50 mM imidazole in Buffer B. As before, imidazole was removed, as described earlier. Proteins were confirmed by SDS PAGE and Western blot using NYVAC-positive sera.

Detection of Antibody Response.

ELISA was carried out with *E. coli-purified* monkeypox proteins as a solid-phase bound antigen. Ninety-six-well microtiter plates were coated with either purified monkeypox A27Lo, A33Ro, B5Ro, or L1Ro at a concentration of 50 ng per well in coating buffer (50 mM $NaHCO_3$, pH 9.6). The plates were blocked with post-coating buffer (5% sucrose, 1.25% nonfat dry milk, and 2.5% BSA) for 1 h at 21° C. Serial dilutions of the monkey sera in Dilsim II (BioMerieux, Paris, France) were applied and incubated for 1 h at 37° C. After washing, 1:60,000 peroxidase goat anti-human IgG (Kirkegaard & Perry Laboratories, Gaithersburg, Md.) was applied and the plates were incubated for an additional hour at 37° C. followed by washing. The plates were developed by the addition of Enhanced K-Blue (Neogen, Lexington, Ky.) and incubated at 21° C. for 15 min. The colorimetric assay was stopped by adding 2N $H_2SO_4$. Absorbance values were measured at 450 nm on a microtiter plate reader (BioTek, Winooski, Vt.). All tested samples were assayed in duplicate. Results of the ELISA were expressed as endpoint titers, calculated as the reciprocal values of the lowest dilution with an OD of 0.3, which is the equivalent of twice the OD mean pre-immune serum samples at a dilution of 1:50 dilution.

In a procedure modified from Boyce et al. (24) kinetic ELISA assay was performed coating plates at 50 ng/well (0.05 M Na carbonate buffer, pH 9.6) with either one of the purified monkeypox proteins listed above or one of four homologous vaccinia proteins (A27L, A33R, B5R, and L1R) produced from baculovirus and obtained from Drs. Gary H. Cohen and Roselyn J. Eisenberg at the University of Pennsylvania (Philadelphia, Pa.). Duplicate wells were coated with 100 μl of the diluted antigen, and 100 μl of carbonate buffer was added to an additional well for each sample to be tested. Plates were coated overnight at 4° C. Nonspecific adsorption was prevented with 200 μl/well of blocking buffer (2% nonfat dry milk) for 1 h at 37° C. After washing (BioTek) with wash buffer (0.02% Tween-20 in PBS), 100 μl of diluted test sera (1:100 in blocking buffer) were added to each well in triplicate (two coated wells and one uncoated well). Plates were incubated for 1 h at 37° C., washed four times, and incubated for 1 h at 37° C. with 1:10,000 dilution of HRP-conjugated goat antihuman IgG antibody (Jackson ImmunoResearch Laboratories, West Grove, Pa.). Plates were washed with wash buffer four times followed by distilled water. One hundred μl of Super AquaBlue ELISA substrate (eBioscience, San Diego, Calif.) was added to each well and plates were read immediately using a Dynex Technologies microplate reader (Chantilly, Va.). The rate of color change in mOD/min (mOD: milli-optical density) was read at a wavelength of 405 nm every 9 s for 5 min with the plates shaken before each measurement. The mean mOD/min reading of duplicate wells was calculated, and the background mOD/min was subtracted from the corresponding well.

Intracellular Cytokine Staining.

Frozen PBMC were thawed and incubated overnight in a 37° C./5% $CO_2$ incubator in RPMI/20% FCS. In a ninety-six-well plate, $10^6$ cells were incubated in 0.2 ml RPMI/10% FCS for 1 h at 37° C. in the absence or presence of a pool of overlapping peptides (two hundred seven total peptides) of monkeypox proteins A33Ro, A27Lo, L1Ro, and B5Ro (1 μg/ml each) supplemented with costimulators CD28 and CD49d (1 μg/ml each). After addition of 10 μg/ml Brefeldin A (Sigma), cells were incubated for 5 h at 37° C. and processed for surface and intracellular cytokine staining. Briefly, cells were washed with 1% FCS in PBS, surface-stained for 30 min with CD4-PerCP and CD8β-PE (2 μl each) (Becton-Dickinson, Franklin Lakes, N.J.), washed again, and permeabilized with FACSPerm (BD Pharmingen, San Diego, Calif.) for 10 min at room temperature in the dark. Following two further washes, cells were intracellularly stained with anti-TNF-α, anti-IFN-γ (both APC-conjugated) (2 μl/well each) (BD Pharmingen), and FITC-conjugated anti-IL-2 (4 μl/well each) (BD Pharmingen). Cells were incubated for 30 min at 37° C., fixed with 200 μl 1% paraformaldehyde (Sigma) in PBS, and analyzed by four-color flow cytometry (FACSCalibur-Multiwell Plate Manager, Becton-Dickinson).

Results

Generation of Monkeypox Immunogens and Study Design.

To assess whether a subunit vaccine could confer protection from monkeypox, we expressed four monkeypox virus proteins in *E. coli*. The cDNAs encoding the monkeypox protein orthologs to the VACV L1R, A33R, and B5R gene products were first modified by deleting their transmembrane region (FIG. 1A) to optimize expression and purification in *E. coli*. In contrast, the A27Lo protein was expressed from the unmodified cDNA. All purified proteins were used either alone or in conjunction with the corresponding native cDNA plasmids to immunize healthy rhesus macaques. Two groups of macaques (groups 1 and 4) were immunized by the intramuscular and intradermal routes with the unmodified DNA plasmids encoding the EEV monkeypox proteins A33Ro and B5Ro and the IMV proteins A27Lo and L1Ro (FIG. 1A). Group 1 was boosted by the intramuscular route with all the recombinant proteins, which for simplicity are designated with the same nomenclature as the VACV proteins A27L, A33R, B5R, and L1R with the addition of an 'o' that stands for ortholog, adjuvanted with CpG. Two additional groups were immunized with the recombinant protein alone either in CpG (group 2) or alum (group 3) to assess the relative ability of proteins alone with the two different adjuvants to elicit protective antibody responses. One control animal (in group 5) was mock-immunized with a combination of alum and CpG (FIG. 1B).

Binding Antibodies Specific for A33Ro, B5Ro, A27Lo, and L1Ro.

The antibody response to the four monkeypox recombinant proteins in the immunized animals was studied using ELISA with endpoint dilution or kinetic readout. DNA immunization alone elicited low levels of binding antibodies to all four immunogens (FIG. 2A). In contrast, two boosts of DNA-primed animals with the four recombinant proteins elicited high levels of antibodies whose titers were higher than those elicited by two immunizations with proteins alone, regardless of the adjuvant used except in the case of L1Ro (FIG. 2A). Indeed, 2 weeks after the last immunization, the macaques immunized with DNA prime/protein boost had the highest antibody titers to three of the four monkeypox proteins. A similar pattern was observed in the kinetic ELISA (data not shown). At 1 week before challenge exposure to monkeypox, the wide range of the antibody titers to A33Ro across the groups that were immunized with proteins was significant (P=0.017 by the exact Kruskal-Wallis test corrected for multiple testing), but no other significant differences in the titers of binding antibodies among these three groups were observed (P>0.50). Each of these groups had substantially higher antibody titers than animals immunized with DNA only (Table I), making the differences over all four groups significant with one minor exception (P<0.06 for each protein). Using kinetic ELISA assay, the antibody responses to monkeypox proteins were compared to the responses of the corresponding proteins from vaccinia. There was a strong correlation (R=0.95; P<0.001) between the homologous proteins (FIG. 2B) indicating that inducing monkeypox-specific responses will provide cross-reactive antibodies to vaccinia.

Neutralizing Antibodies to IMV and EEV Forms Induced by Vaccination.

Neutralizing antibody titers to the IMV form of VACV were measured using either a β-Gal-based assay or a plaque reduction assay. The plaque reduction assay was also used to measure neutralizing antibodies to the IMV form of monkeypox virus. In the case of EEV, neutralizing activity was measured using a novel monkeypox virus EEV spread inhibition assay. Macaques immunized with DNA only had no serum neutralizing antibodies in any of these assays (Table II) whereas all animals in other groups developed neutralizing antibody titers to VACV and monkeypox virus IMV. Overall, reasonable consistency was found in VACV neutralizing assays using the β-Gal and the plaque reduction assay (Table II). Importantly, sera positive in the VACV assays also had neutralizing activity to the IMV form of monkeypox (P=0.0054 by the exact Spearman rank correlation method in groups 1, 2, and 3). Differences in neutralizing antibody titers among groups 1, 2, and 3 were not significant.

To assess whether immunization with B5Ro and A33Ro, the proteins specific for the EEV form, elicited neutralizing antibodies to EEV, we performed a monkeypox EEV spread inhibition assay. With this assay, no inhibition was found in sera from animals immunized with DNA alone, whereas all the sera of animals immunized with the DNA prime/protein boost regimen and some of those immunized with proteins alone inhibited monkeypox virus EEV spread (Table II). The variation across groups 1, 2, and 3 is significant (P=0.021 by the exact Wilcoxon-Gehan test corrected for multiple comparisons).

TABLE I

Humoral immune response in macaques before monkeypox virus challenge[a]

| Macaque | Treatment | Binding Ab Titers to Monkeypox Proteins Prevaccination/Prechallenge | | | |
|---|---|---|---|---|---|
| | | L1Ro | B5Ro | A33Ro | A27Lo |
| Group 1 482 | DNA + protein- | 50/17,820 | 50/74,300 | 50/60,420 | 50/59,340 |

TABLE I-continued

Humoral immune response in macaques before monkeypox virus challenge[a]

| Macaque | Treatment | Binding Ab Titers to Monkeypox Proteins Prevaccination/Prechallenge | | | |
|---|---|---|---|---|---|
| | | L1Ro | B5Ro | A33Ro | A27Lo |
| 489 | CpG | 50/15,120 | 50/72,190 | 50/30,000 | 50/70,570 |
| 496 | | 50/12,790 | 50/26,090 | 50/22,940 | 50/12,930 |
| Group 2 | Proteins- | | | | |
| 498 | CpG | 50/7,820 | 50/27,090 | 50/11,630 | 50/7,900 |
| 499 | | 50/12,260 | 103/62,980 | 50/14,050 | 50/13,100 |
| 500 | | 50/14,000 | 50/21,970 | 50/9,190 | 50/7,290 |
| 501 | | 50/20,760 | 50/56,660 | 50/26,410 | 50/21,230 |
| Group 3 | Proteins + | | | | |
| 480 | Alum | 50/14,060 | 50/25,300 | 50/3,630 | 50/14,240 |
| 481 | | 50/18,620 | 50/69,050 | 50/5,810 | 12/36,840 |
| 497 | | 50/10,660 | 50/7,880 | 50/2,380 | 50/6,160 |
| Group 4 | DNA | | | | |
| 479 | | 50/50 | 50/50 | 50/190 | 50/80 |
| 488 | | 50/50 | 50/30 | 50/270 | 50/60 |
| 491 | | 50/50 | 127/180 | 50/50 | 50/240 |

[a]Titers of ELISA-binding Abs in monkey sera before vaccination and 1 wk before challenge exposure. Values were calculated from duplicate assays.

Vaccination-Induced T Cell Response.

Figure 3A:
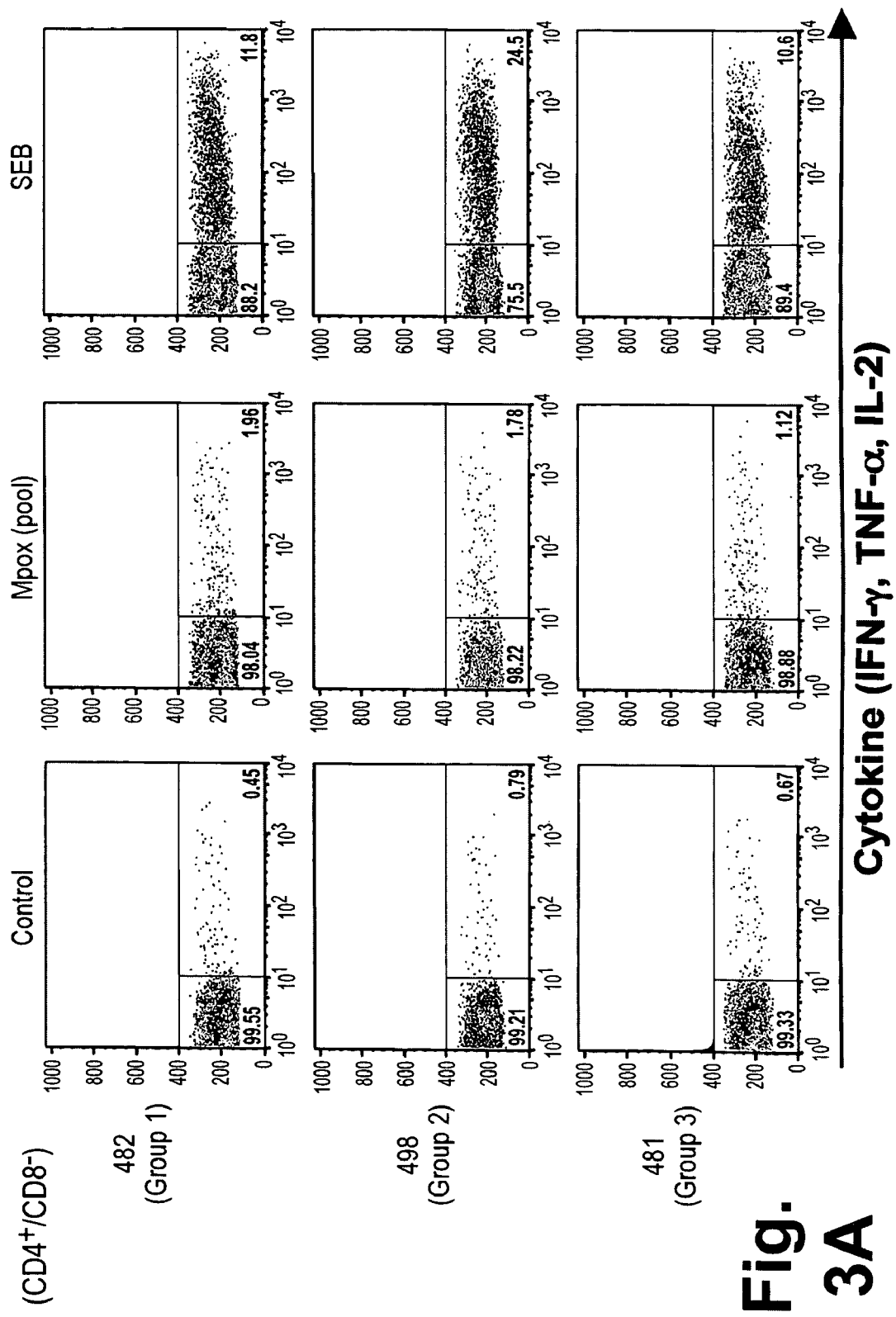
FIG. 3: $CD4^+$ and $CD8^+$ T cell responses. A and B: Representative data from blood of animals 482, 498, and 481 at 2 weeks after the last immunization. C: Percentage of $CD4^+$ and $CD8^+$ T cells that express IL-2 or IFM-γ and TNF-α after stimulation with the peptide pools derived from the A27Lo, A33Ro, B5Ro, and L1Ro proteins at week 0 and 3 weeks (post-immunization) before challenge exposure to monkeypox virus. The columns represent the mean percentage of positive cells after subtraction of the background, with error bars extending one standard deviation. P values were obtained using Student's paired t-test, with a two-tailed distribution.
Figure 3B:
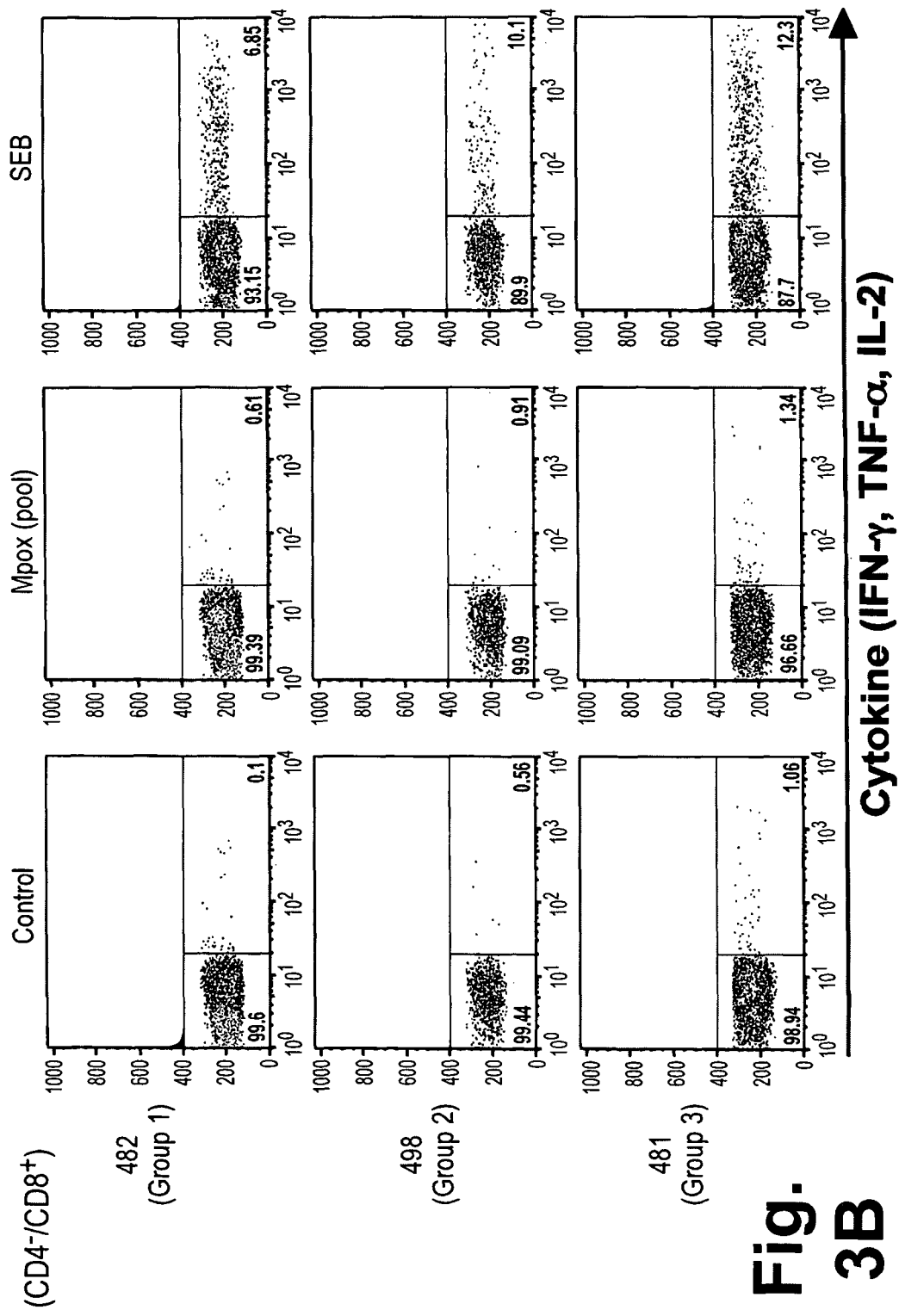

The overall T cell responses were measured by intracellular cytokine staining following specific stimulation with a pool of overlapping peptides encompassing the four proteins used as immunogens. The ability of CD8+ and CD8− T cells to produce cytokines was assessed by flow cytometry. Staphylococcal enterotoxin B (SEB) stimulation was used as a positive control to assess the ability of the cells to respond to antigens. Representative raw data of virus-specific CD8− and CD8+ T cell response (expression of IFN-γ, TNF-α, and IL-2) are provided for animals 482, 498, and 481 at 2 weeks after the last immunization (FIG. 3A, 3B). Thereafter, the mean percentage of CD8− and CD8+ T cells producing IL-2 or IFN-γ and TNF-α in the various groups was measured at week 0 and 3 weeks before challenge exposure (FIG. 3B). Overall, CD4+ T cell responses tended to be higher than CD8+ T cell responses, consistent with the ability of DNA and proteins to induce helper response. The variation over the groups in the CD8− (CD4+) T cell response measured as the ability of T cells to produce IFN-γ and TNF-α was significant (P=0.042 by the exact Kruskal-Wallis test corrected for multiple tests), due primarily to the higher responses in the macaques that received DNA plus proteins than those in all other groups. Only animals from groups 1 and 2 showed a significant increase of IL-2 in both CD4+ (P=0.0021 and P=0.0019, respectively) and CD8+ (P=0.037 and P=0.029, respectively) T cell responses compared to other groups before or after immunization. Group 1 also showed a significant increase of TNF-α/IFN-γ in CD4+ T cells but not in CD8+ T cells. In some animals, the background level of cytokine production in samples obtained before immunization precluded proper assessment of CD4+ and CD8+ T cell response.

Subunit Vaccine Confers Protection Against Lethal Monkeypox Virus Challenge.

Macaques in groups 1, 4, and 5 were challenged 5 weeks after the last protein boost with $5 \times 10^7$ pfu of monkeypox virus (Zaire 79 strain) intravenously. Groups 2 and 3 were challenged identically but 4 weeks after the last protein boost. The virological and clinical outcomes post-challenge were assessed by monitoring the number of skin lesions, the health status (10, 11, 25), and by measuring DNA viral genomes in blood by quantitative real-time PCR DNA assay (20). Macaques immunized with the DNA prime/protein boost regimen had a mild disease according to the World Health Organization scoring system with a lesion number of less than twenty-five (Table III). Importantly, in most of these animals, papules did not evolve to vesicles and disappeared within a few days. In the two groups immunized with proteins together with either CpG or alum, two animals had mild disease, three moderate (25-99), two severe (100-200), and none grave (>200). All animals from these groups completely resolved their lesions (Table III). In contrast, all macaques immunized with DNA developed innumerable lesions that progressed from papules to vesicles to pustules. The animals were euthanized at days 11, 17, and 21 post-infection (Table III). Thus, macaques immunized with subunit vaccines based on four monkeypox proteins with or without DNA priming were protected from a lethal injection of monkeypox virus. Among these groups, however, animals immunized with a combination of DNA and proteins fared much better. Quantitative analysis of the monkeypox DNA genomes in blood demonstrated equivalent exposure to monkeypox in all animals (Table IV). Following exposure, monkeypox genomes were detectable mainly in macaques immunized with DNA only (Table IV), consistent with the overall clinical findings (Table III).

TABLE III

Clinical outcome of monkeypox challenge exposure[a]

| Macaque | Treatment | Pox Lesion Count | | | | | | | | |
|---|---|---|---|---|---|---|---|---|---|---|
| | | Day 0 | Day 2 | Day 4 | Day 7 | Day 9 | Day 11 | Day 14 | Day 17 | Day 21 |
| Group 1 | DNA + proteins-CpG | | | | | | | | | |
| 482 | | 0 | 0 | 0 | 6 | 4 | 3 | 0 | 0 | 0 |
| 489 | | 0 | 0 | 0 | 15 | 0[a] | 0 | 0 | 0 | 0 |
| 496 | | 0 | 0 | 4 | 3 | 3 | 0 | 0 | 0 | 0 |
| Group 2 | Proteins-CpG | | | | | | | | | |
| 498 | | 0 | 0 | 5 | 37 | 37 | 36 | 31 | 0[a] | 0 |
| 499 | | 0 | 0 | 2 | 22 | 37 | 37 | 4 | 0[a] | 0 |
| 500 | | 0 | 0 | 6 | 108 | 120 | 120 | 24 | 0[a] | 0 |
| 501 | | 0 | 0 | 0 | 14 | 20 | 20 | 1 | 0[a] | 0 |
| Group 3 | Proteins + Alum | | | | | | | | | |
| 480 | | 0 | 0 | 0 | 2 | 31 | 31 | 5 | 0[a] | 0 |
| 481 | | 0 | 0 | 1 | 5 | 13 | 22 | 0[a] | 0 | 0 |
| 497 | | 0 | 0 | 11 | 148 | 148 | 155 | 5 | 0[a] | 0 |
| Group 4 | DNA | | | | | | | | | |
| 479 | | 0 | 0 | TNTC | TNTC | TNTC | [b] | | | |

TABLE III-continued

Clinical outcome of monkeypox challenge exposure[a]

| Macaque | Treatment | Pox Lesion Count | | | | | | | | |
|---|---|---|---|---|---|---|---|---|---|---|
| | | Day 0 | Day 2 | Day 4 | Day 7 | Day 9 | Day 11 | Day 14 | Day 17 | Day 21 |
| 488 | | 0 | 0 | 6 | TNTC | TNTC | TNTC | TNTC | TNTC | TNTC |
| 491 | | 0 | 0 | TNTC | TNTC | TNTC | TNTC | [b] | | |
| Group 5 | CpG + Alum | | | | | | | | | |
| 485 | | 0 | 0 | TNTC | TNTC | TNTC | [b] | | | |

[a]Macaques were challenged with $5 \times 10^7$ PFU of monkeypox Zaire 79 by the i.v. route. Characteristic pox lesions (whether papular, vesicular, or scabs[a]) were counted on the whole body of each animal. When the number of lesions were too numerous to count (TNTC), and when vital signs were critical, animals were euthanized ([b]).

TABLE IV

Viral genomes in blood following monkeypox challenge exposure[a]

| Macaque | Treatment | Monkeypox Virus Genomes/ ml Blood (log 10) | | | | |
|---|---|---|---|---|---|---|
| | | 3 min | Day 2 | Day 4 | Day 7 | Day 9 |
| Group 1 | DNA + proteins-CpG | | | | | |
| 482 | | 6.4 | <3.6 | <3.6 | <3.6 | <3.6 |
| 489 | | 5.6 | <3.6 | <3.6 | <3.6 | <3.6 |
| 496 | | 6.2 | <3.6 | 3.7 | <3.6 | <3.6 |
| Group 2 | Proteins-CpG | | | | | |
| 498 | | 5.8 | <3.6 | <3.6 | <3.6 | <3.6 |
| 499 | | 5.8 | <3.6 | <3.6 | <3.6 | <3.6 |
| 500 | | 5.5 | <3.6 | <3.6 | <3.6 | <3.6 |
| 501 | | 6.1 | <3.6 | <3.6 | <3.6 | <3.6 |
| Group 3 | Proteins + Alum | | | | | |
| 480 | | 5.5 | <3.6 | <3.6 | <3.6 | <3.6 |
| 481 | | 6.1 | <3.6 | <3.6 | <3.6 | <3.6 |
| 497 | | 5.6 | <3.6 | <3.6 | <3.6 | <3.6 |
| Group 4 | DNA | | | | | |
| 479 | | 6.0 | <3.6 | 4.3 | 6.3 | 7.4 |
| 488 | | 6.9 | <3.6 | <3.6 | <3.6 | 7.4 |
| 491 | | 5.8 | <3.6 | 3.7 | 7.4 | 7.4 |
| Group 5 | CpG + Alum | | | | | |
| 485 | | 6.5 | 4.5 (day 3) | 5.6 (day 6) | 5.6 | 7.2 |

[a]The limit of detection is 5000 copies/ml of blood. All prechallenge samples were below detection.

Correlates of Protection.

As we had observed a significant difference between CD4+ T cell responses in the animals that fared better following monkeypox virus exposure, we performed a regression analysis of the percentage of virus-specific CD4+ T cells at the time of monkeypox virus challenge and the number of lesions that developed following exposure. A significant negative correlation was found between the percentage of IL-2-producing and IFN-γ/TNF-α-producing CD4+ T cells and lesion number (R=−0.71, P=0.0083; R=−0.68, P=0.013, respectively), suggesting the importance of the induction of a Th1 helper response (FIG. 4A, 4B).

Figure 5:
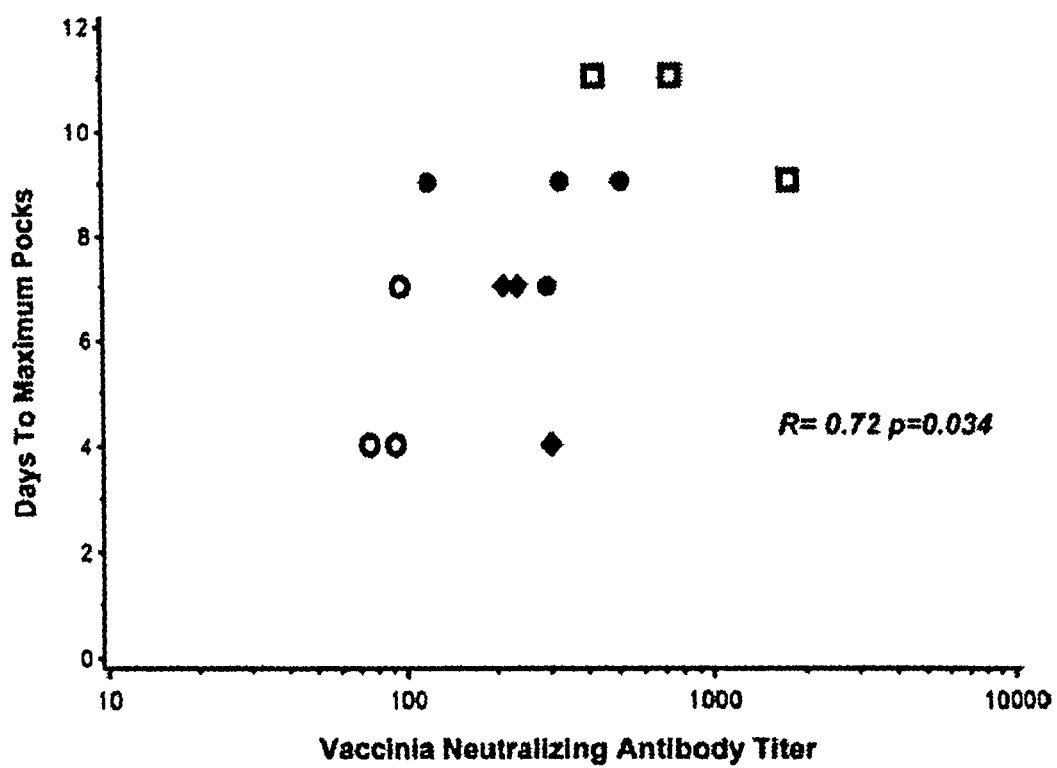
FIG. 5: Regression analysis of IMV VACV neutralizing antibody titers and time to maximum number of pox lesions. Open circle=animal from the group immunized with DNA. Closed circle=animal from the group immunized with protein plus CpG. Open square=animal from the group immunized with protein plus alum. Diamond=animal from the group immunized with DNA plus proteins.
Figure 6:
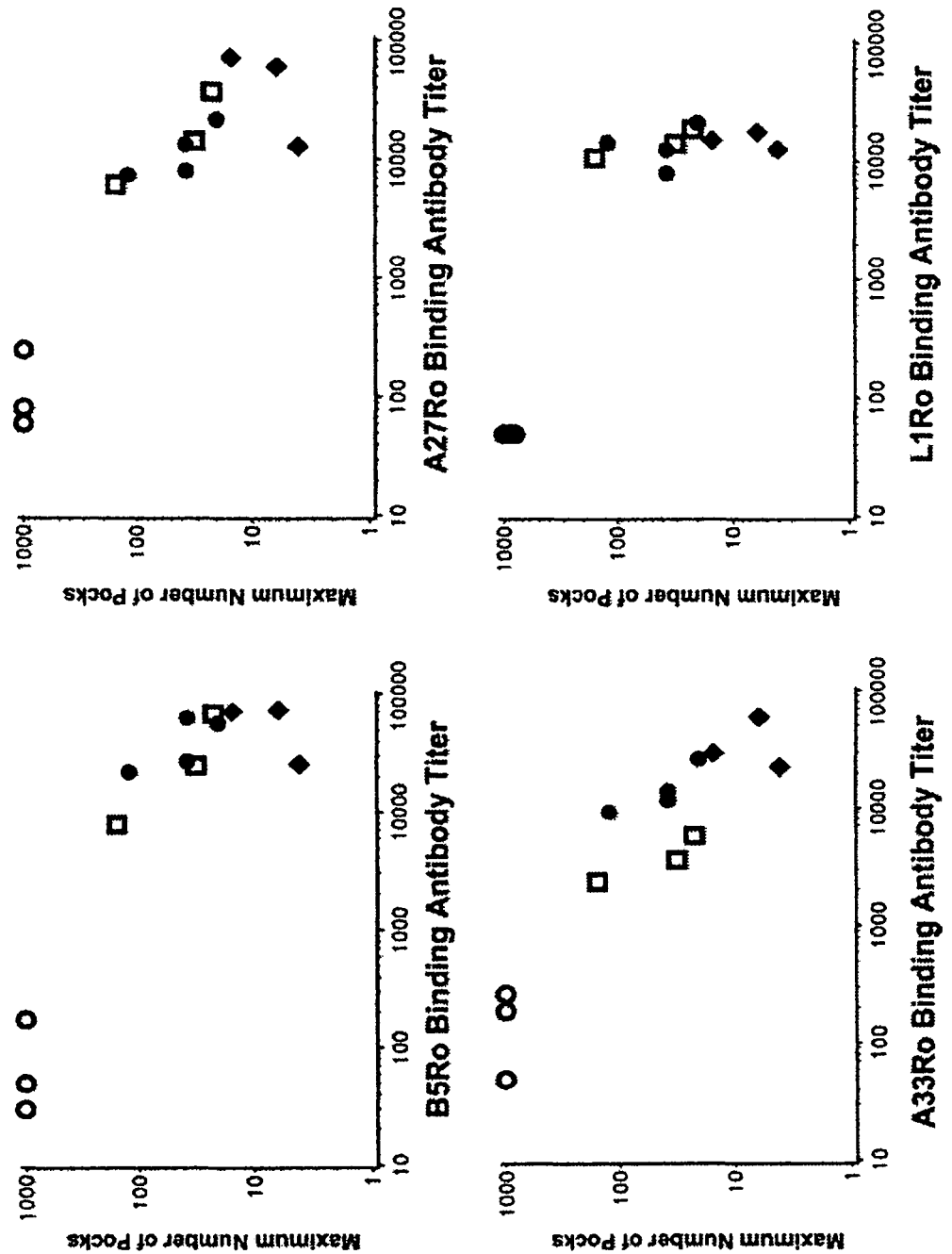
FIG. 6: Regression analysis of maximum number of pocks and antibody titers to L1Ro, B5Ro, A33Ro, and A27Lo. Open circle=animal from the group immunized with DNA. Closed circle=animal from the group immunized with protein plus CpG. Open square=animal from the group immunized with protein plus alum. Diamond=animal from the group immunized with DNA plus proteins. Lesions too numerous to count were assigned the value 1000 for plotting.

To establish the role of antibodies in protection from disease, titers of neutralizing antibodies to VACV (measured with the β-Gal assay) and monkeypox as well as binding antibody titers to A27Lo, A33Ro, B5Ro, and L1Ro (Table I) were analyzed with respect to the time of lesion development and the maximum number of lesions. Neutralizing antibody titers to the IMV form of VACV did not correlate with the maximum number of pocks but correlated significantly (R=0.72, P=0.034) with the time of appearance of pocks (FIG. 5), suggesting that the extent of neutralizing antibodies to IMV may contribute to the delay in the appearance of skin lesions. In contrast, the titer of binding antibody induced by vaccination to all four monkeypox proteins inversely correlated with the maximum lesion number (P<0.01 for all groups, Spearman correlation coefficients ranging from −0.80 to −0.88), suggesting that binding antibodies with this specificity participate in the containment of pocks (FIG. 6). Since each animal's binding antibody titers tended to be high or low across all four proteins (correlation coefficients between pairs of titers ranging from 0.72 to 0.95), each trend in FIG. 6 was adjusted for these correlations in a rank-based partial correlation analysis. The results suggested that the A33Ro titer was the most strongly related to the number of pocks and that the correlation of the B5Ro titer was the most weakly related to the number of pocks, but more tests should be conducted with more animals, ideally.

Figure 7:
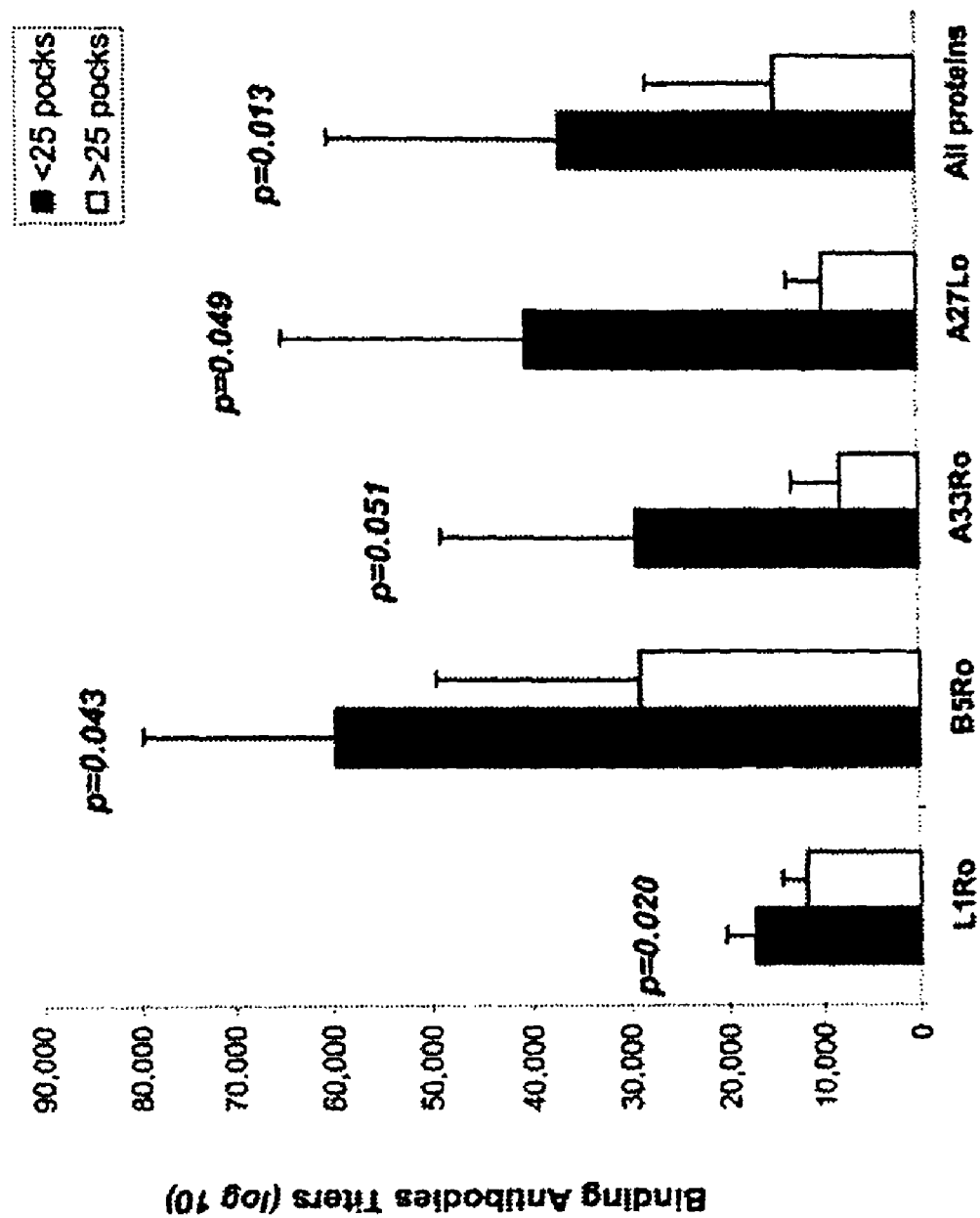
FIG. 7: Sera from animals 1 week before challenge were tested for the presence of binding antibodies to different proteins (L1Ro, B5Ro, A33Ro, and A27Lo). According to the World Health Organization scoring system, monkeys were divided into two groups: animals with mild disease (<25 pocks) and animals with moderate to severe disease (25-200 pocks). Each column represents the average of the response of the animals in each group to each protein or to the average by animal over all proteins, with error bars extending one standard deviation. P values were obtained using the t test with Satterthwaite's approximation for unequal variances.

As we observed a correlation between the extent of binding antibodies and severity of disease, we tested for and found significant differences in antibody titers in the animals that had mild (fewer than twenty-five pocks) or moderate/severe disease (more than twenty-five lesions but fewer than two hundred). The animals were divided into two groups according to their lesion number (Table V). A significant difference in mean binding titers to L1Ro, B5Ro, and A27Lo was found between the groups that had mild or moderate/severe disease (FIG. 7). In the case of A33Ro, the difference between the two groups only approached statistical significance. A significant difference was found between the two groups when the titers to all proteins were averaged for each animal and analyzed (P=0.013), providing further support to the importance of antibodies in protecting from lethal monkeypox (FIG. 7). A similar correlation with disease severity was seen when the protein-specific antibody responses were measured in the kinetic ELISA; L1Ro: P=0.22, B5Ro: P=0.047, A27Lo: P=0.028, and A33Ro: P=0.006.

TABLE V

Binding Ab titers to monkeypox correlated with the maximum number of lesions[a]

| Disease | Macaque | Treatment | Maximum Number of Pocks | Binding Ab Titers to Monkeypox Proteins | | | |
|---|---|---|---|---|---|---|---|
| | | | | L1Ro | B5Ro | A33Ro | A27Lo |
| Mild | 496M | DNA + Proteins-CpG | 4 | 12,790 | 26,090 | 22,940 | 12,930 |
| | 482M | DNA + Proteins-CpG | 6 | 17,820 | 74,300 | 60,420 | 59,340 |

TABLE V-continued

Binding Ab titers to monkeypox correlated with the maximum number of lesions[a]

| Disease | Macaque | Treatment | Maximum Number of Pocks | Binding Ab Titers to Monkeypox Proteins | | | |
|---|---|---|---|---|---|---|---|
| | | | | L1Ro | B5Ro | A33Ro | A27Lo |
| Moderate/severe | 489M | DNA + Proteins-CpG | 15 | 15,120 | 72,190 | 30,000 | 70,570 |
| | 501M | Proteins-CpG | 20 | 20,760 | 56,660 | 26,410 | 21,230 |
| | 481M | Proteins + Alum | 22 | 18,620 | 69,050 | 5,810 | 36,840 |
| | 480M | Proteins + Alum | 31 | 14,060 | 25,300 | 3,630 | 14,240 |
| | 498M | Proteins-CpG | 37 | 7,820 | 27,090 | 11,630 | 7,900 |
| | 499M | Proteins-CpG | 37 | 12,260 | 62,980 | 14,050 | 13,100 |
| | 500M | Proteins-CpG | 120 | 14,000 | 21,970 | 9,190 | 7,290 |
| | 497M | Proteins + Alum | 155 | 10,660 | 7,880 | 2,380 | 6,160 |

[a]According to the World Health Organization scoring system, monkeys were divided into two groups: animals with mild disease (<25 pocks) and animals with moderate to severe disease (25-200 pocks).

B Cell Epitopes Recognized by the Immunized Macaques.

Figure 8A:
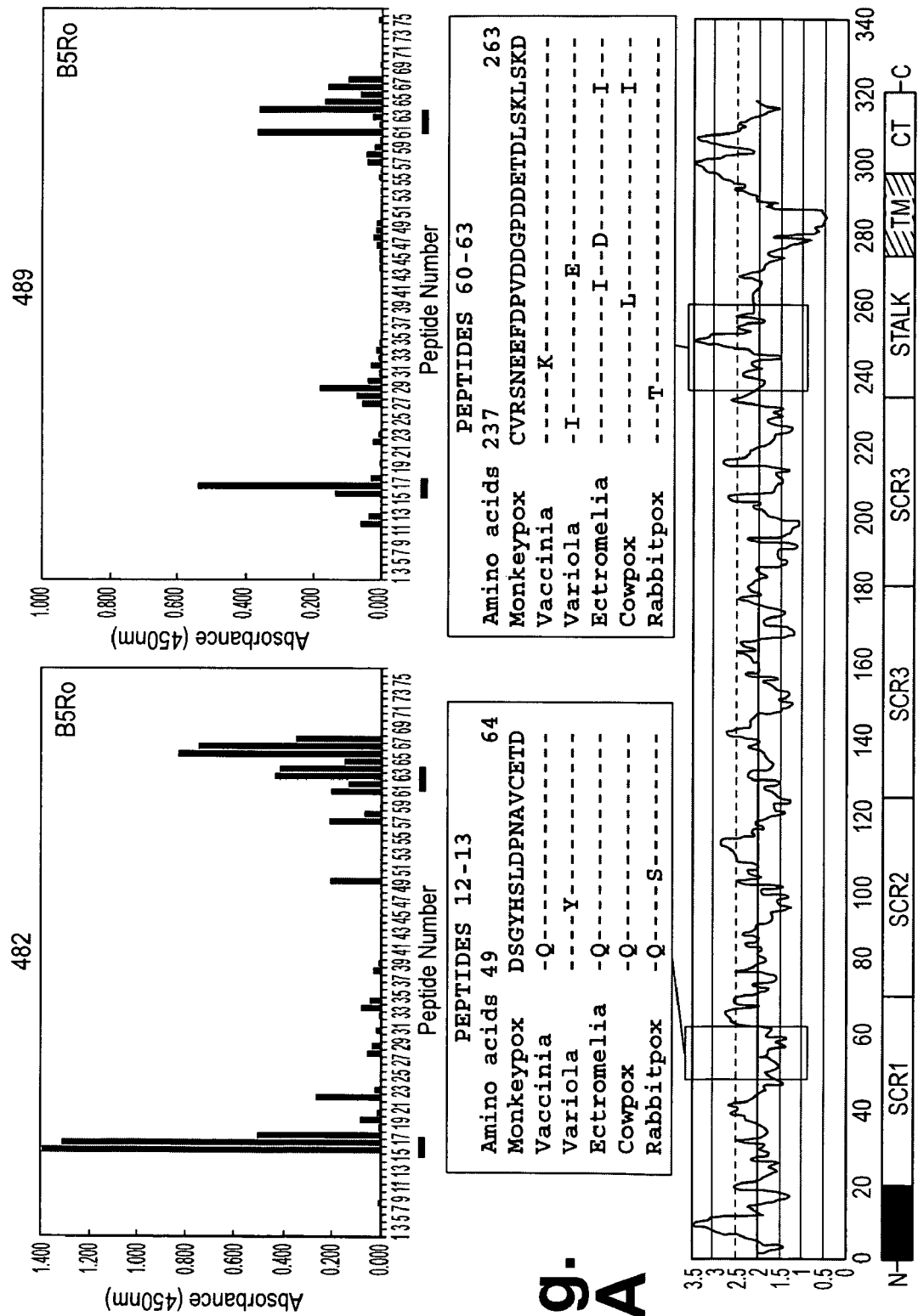
FIG. 8: Identification of B cell epitopes. Peptide scans were performed by ELISA for the B5Ro protein (A), A33Ro (B), and L1Ro (C). In the middle of each figure the amino acid sequence in a single letter amino acid code is given for related orthopoxviruses. On the bottom, B cell-predicted epitopes obtained from the BcePred software (35). In (A), for Peptides 12-13, the sequence identifiers are assigned as follows: Monkeypox, SEQ ID NO:14; Vaccinia, SEQ ID NO:15; Variola, SEQ ID NO:16; Ectromelia, SEQ ID NO:15; Cowpox, SEQ ID NO:15; and Rabbitpox, SEQ ID NO:17. In (A), for Peptides 60-63, the sequence identifiers are assigned as follows: Monkeypox, SEQ ID NO:18; Vaccinia, SEQ ID NO:19; Variola, SEQ ID NO:20; Ectromelia, SEQ ID NO:21; Cowpox, SEQ ID NO:22; and Rabbitpox, SEQ ID NO:23. In (B), the sequence identifiers are assigned as follows: Monkeypox, SEQ ID NO:24; Vaccinia, SEQ ID NO:25; Variola, SEQ ID NO:26; Camelpox, SEQ ID NO:27. In (C), the sequence identifiers are assigned as follows: for Peptides 18-20, Monkeypox/Vaccinia/Variola, SEQ ID NO:28; for Peptides 35-36, Monkeypox/Vaccinia/Variola, SEQ ID NO:29.
Figure 8B:
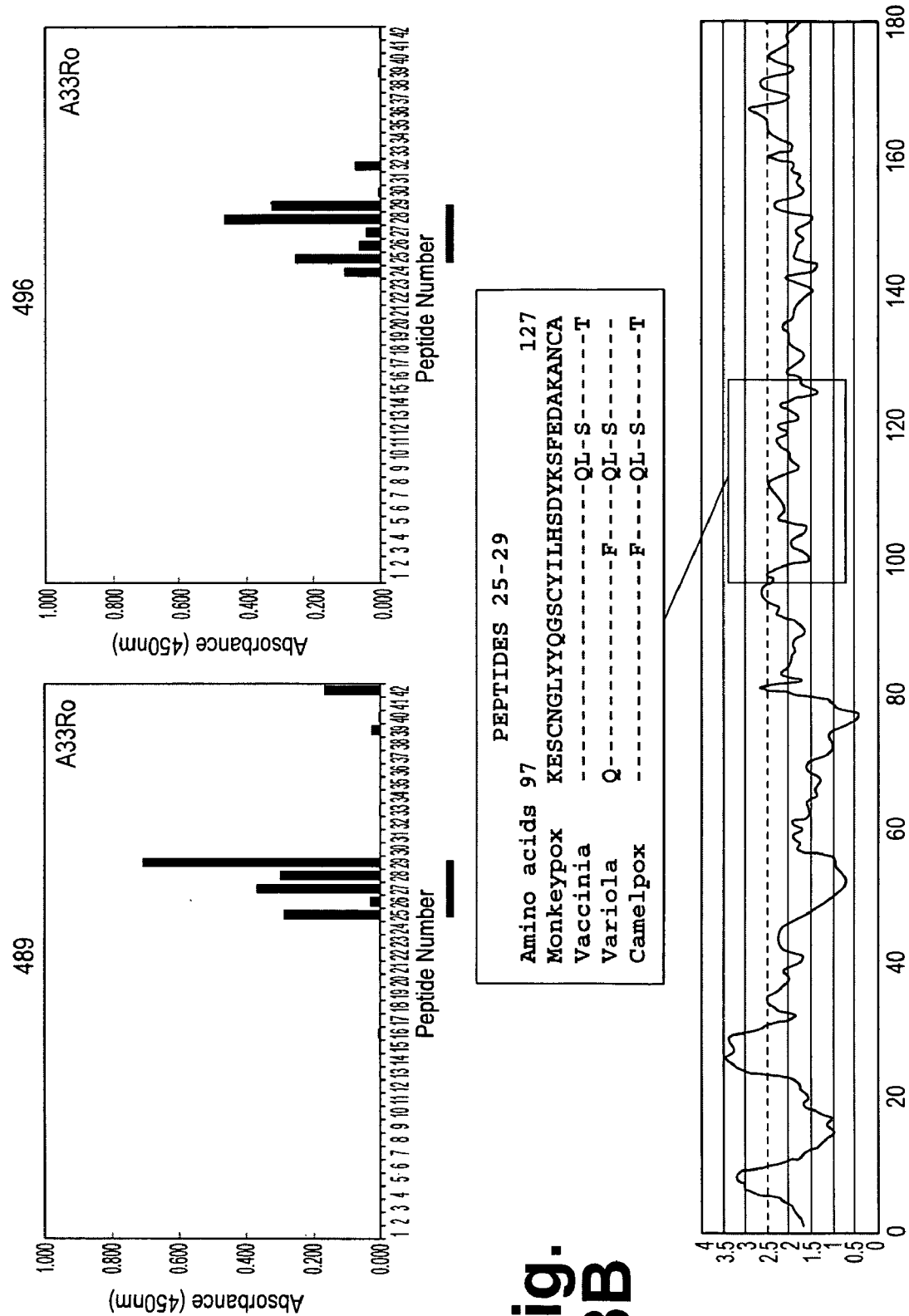
Figure 8C:
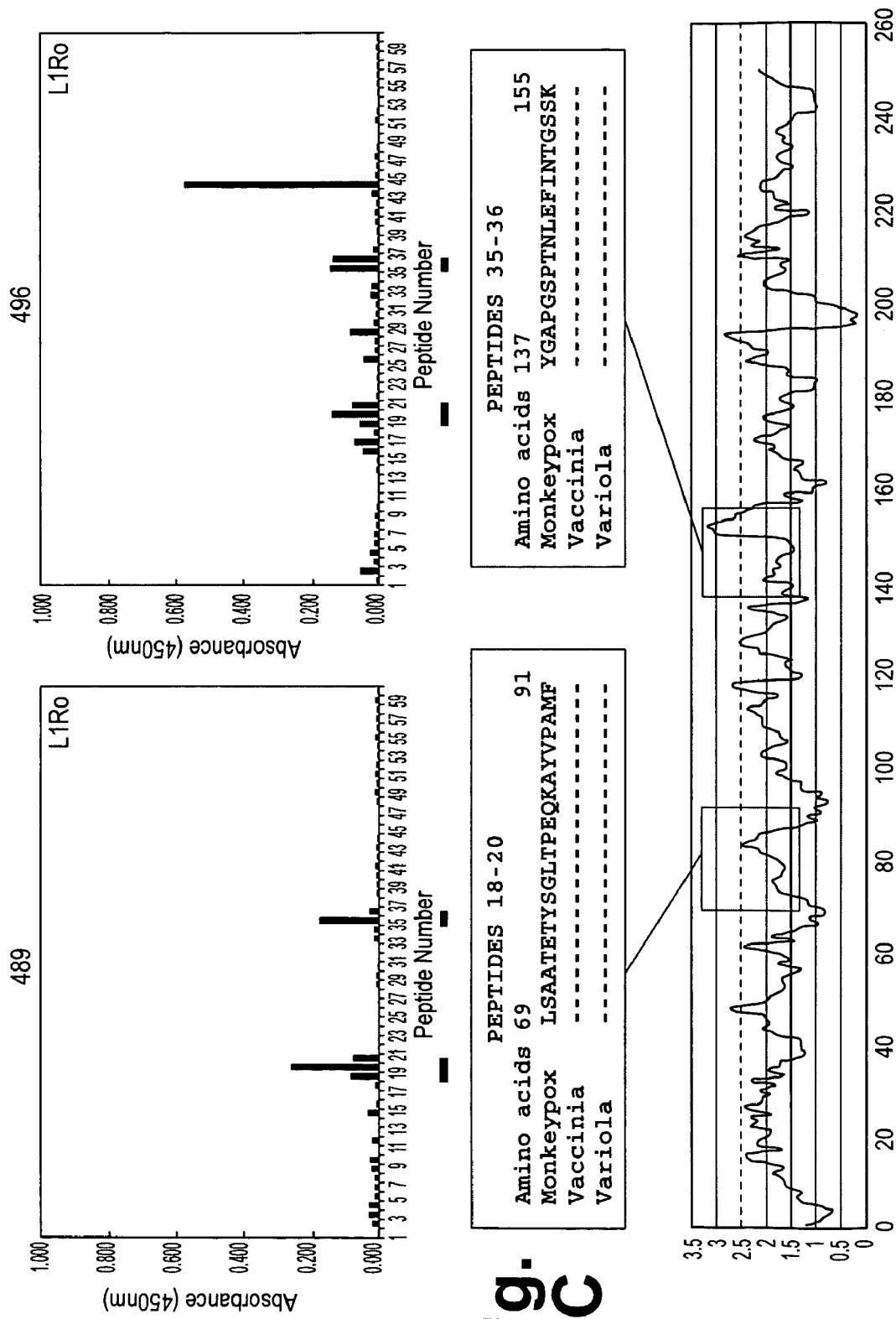
Figure 9:
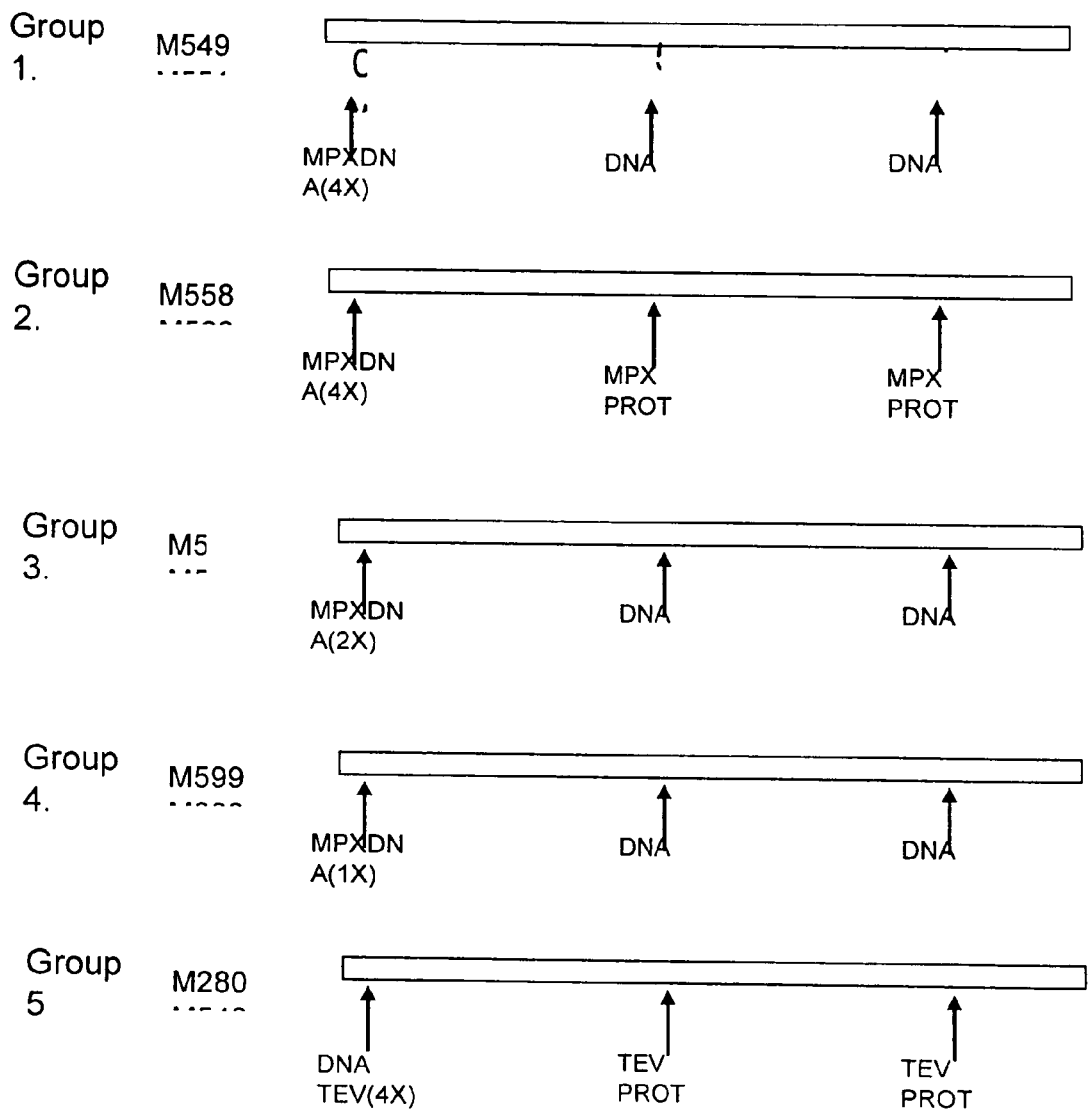
FIG. 9: Experimental design for monkey study, with a single DNA vaccine prime vaccination, followed by two booster vaccinations of protein vaccine. Five groups of 2 rhesus macaques each were vaccinated on week 0 with 1, 2, or 4 doses (1×, 2×, 4×) of a combination of 4 plasmids encoding the monkeypox L1Ro, A33Ro, B5Ro, and A27Lo genes (MPXDNA), or the equivalent of 4 doses of an irrelevant plasmid (TEV) as a negative control, by electroporation. Groups 1, 3, 4, and 5 received a booster DNA vaccine (same vaccine used on wk 0) on weeks 5 and 11. Group 2 received a booster vaccination on weeks 5 and 11 consisting of a combination of 4 purified proteins (i.e., L1Ro, A33Ro, B5Ro, an A27Lo).
Figure 12:
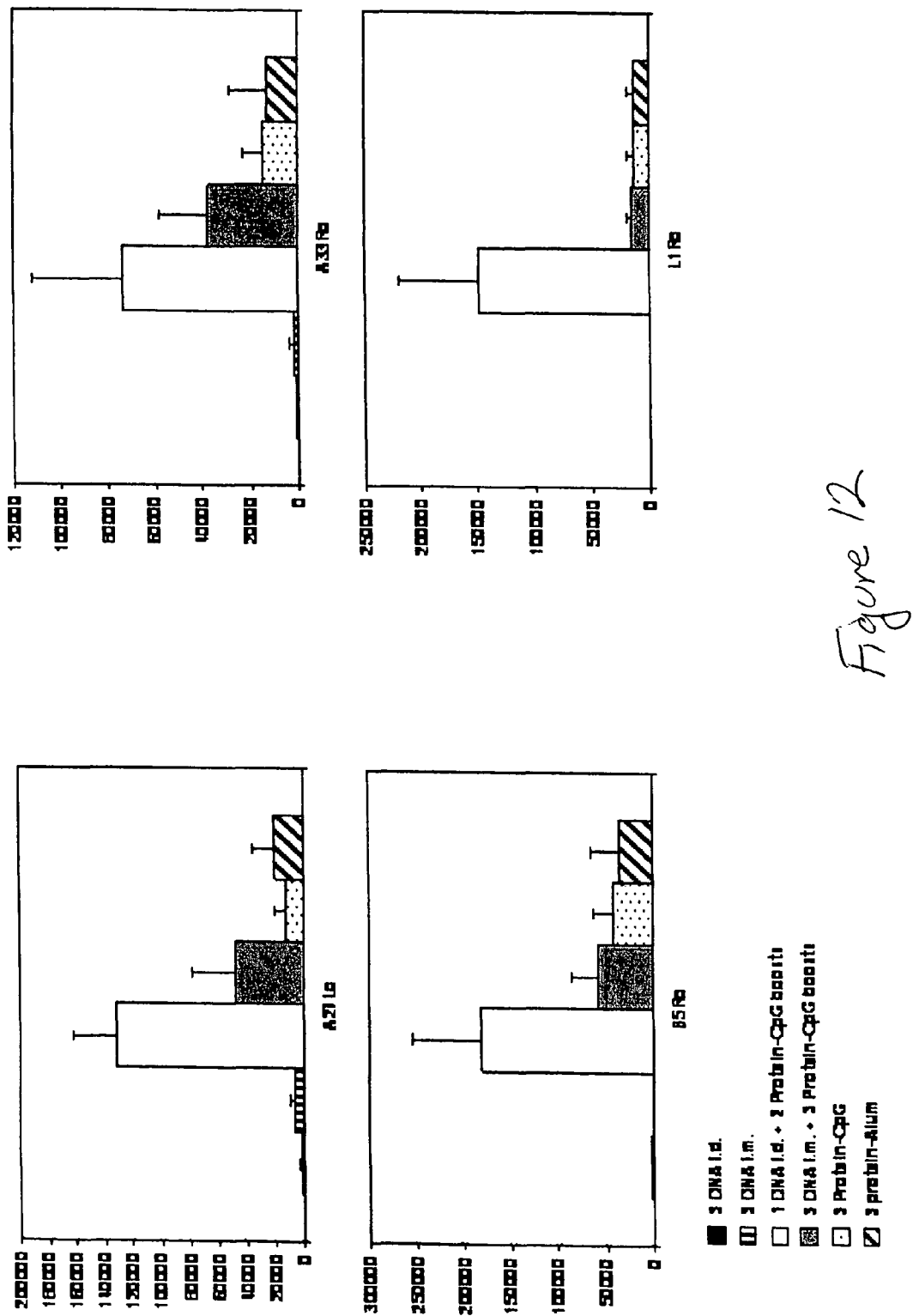
FIG. 12: ELISA antibody responses against the four vaccine immunogens after different immunization regimens. This shows ELISA antibody responses four weeks after the last immunization. Each column represents the mean of the titers for each regimens with the standard deviation. As shown clockwise beginning from the top left, each of A27lo, A33Ro, B5Ro and LiRo was tested with 3 DNA i.d., 3 DNA i.m., 1 DNA i.d+2 protein-CpG boosts, 3 DNA i.d+3 protein-CpG boosts, 3 protein-CpG, and 3 protein-alum.

To identify B cell epitopes recognized by the immunized macaques, we performed ELISA on the macaque sera using overlapping peptides derived from the amino acid sequence of the monkeypox virus B5Ro, A33Ro, L1Ro, and A27Lo proteins. An example of the raw data for these assays is given for B5Ro, A33Ro, and L1Ro on sera of animals from group 1 (FIGS. 8A-8C). Two regions were recognized within the B5Ro protein by the sera of immunized and protected animals: peptides 12-13 (amino acids 49-64) located in the short consensus repeat 1 and peptides 60-63 (amino acids 237-263) that are part of the region adjacent to the transmembrane region defined as STALK (Lyd) (26). Interestingly, several monoclonal antibodies able to neutralize the EEV form of VACV have been mapped to these discontinuous linear epitopes (16, 26-28). The amino acid sequence of these peptides is well conserved among several orthopoxviruses, including VACV and variola virus; however, there are 1-2 amino acid changes in the peptides for every virus evaluated (FIG. 8A).

In the case of A33Ro, a single region spanning peptides 25-29 (amino acids 97-127) is recognized by the sera of protected animals (FIG. 8B). The amino terminus but not the carboxy terminus region of this peptide is highly conserved among orthopoxviruses, including variola. In the case of L1Ro, the sera recognized mainly the regions spanning peptides 18-20 (amino acids 69-91) and peptides 35-36 (amino acids 137-155), which are identical to the VACV and variola virus orthologs (FIG. 8C).

The following references are cited above by number, and the entire contents of these references are incorporated herein by reference. In addition, all the others cited above and not listed below are also entirely incorporated herein by reference.

REFERENCE LIST

1. Jezek, Z., S. S. Marennikova, M. Mutumbo, J. H. Nakano, K. M. Paluku, and M. Szczeniowski. 1986. Human monkeypox: a study of 2,510 contacts of 214 patients. *J. Infect. Dis.* 154:551-555.
2. Jezek, Z., M. Szczeniowski, K. M. Paluku, and M. Mutombo. 1987. Human monkeypox: clinical features of 282 patients. *J. Infect. Dis.* 156:293-298.
3. Hutin, Y. J., R. J. Williams, P. Malfait, R. Pebody, V. N. Loparev, S. L. Ropp, M. Rodriguez, J. C. Knight, F. K. Tshioko, A. S. Khan, M. V. Szczeniowski, and J. J. Esposito. 2001. Outbreak of human monkeypox, Democratic Republic of Congo, 1996 to 1997. *Emerg. Infect. Dis.* 7:434-438.
4. Meyer, H., M. Perrichot, M. Stemmler, P. Emmerich, H. Schmitz, F. Varaine, R. Shungu, F. Tshioko, and P. Formenty. 2002. Outbreaks of disease suspected of being due to human monkeypox virus infection in the Democratic Republic of Congo in 2001. *J. Clin. Microbiol.* 40:2919-2921.
5. CDC. 2003. Multistate outbreak of monkeypox—Illinois, Indiana, and Wisconsin, 2003. *Morb. Mortal. Wkly. Rep.* 52:537-540.
6. Nalca, A., A. W. Rimoin, S. Bavari, and C. A. Whitehouse. 2005. Reemergence of monkeypox: prevalence, diagnostics, and countermeasures. *Clin. Infect. Dis.* 41:1765-1771.
7. Hammarlund, E., M. W. Lewis, S. V. Carter, I. Amanna, S. G. Hansen, L. I. Strelow, S. W. Wong, P. Yoshihara, J. M. Hanifin, and M. K. Slifka. 2005. Multiple diagnostic techniques identify previously vaccinated individuals with protective immunity against monkeypox. *Nat. Med.* 11:1005-1011.
8. CDC. 2001. Vaccinia (smallpox) vaccine: recommendations of the Advisory Committee on Immunization Practices (ACIP), 2001. *Morb. Mortal. Wkly. Rep.* 50:1-26.
9. CDC. 2003. Supplemental recommendations on adverse events following smallpox vaccine in the pre-event vaccination program: recommendations of the Advisory Committee on Immunization Practices. *Morb. Mortal. Wkly. Rep.* 52:282-284.
10. Hooper, J. W., E. Thompson, C. Wilhelmsen, M. Zimmerman, M. A. Ichou, S. E. Steffen, C. S. Schmaljohn, A. L. Schmaljohn, and P. B. Jahrling. 2004. Smallpox DNA vaccine protects nonhuman primates against lethal monkeypox. *J. Virol.* 78:4433-4443.
11. Earl, P. L., J. L. Americo, L. S. Wyatt, L. A. Eller, J. C. Whitbeck, G. H. Cohen, R. J. Eisenberg, C. J. Hartmann, D. L. Jackson, D. A. Kulesh, M. J. Martinez, D. M. Miller, E. M. Mucker, J. D. Shamblin, S. H. Zwiers, J. W. Huggins, P. B. Jahrling, and B. Moss. 2004. Immunogenicity of a highly attenuated MVA smallpox vaccine and protection against monkeypox. *Nature* 428:182-185.
12. Edghill-Smith, Y., D. Venzon, T. Karpova, J. McNally, J. Nacsa, W. P. Tsai, E. Tryniszewska, M. Moniuszko, J. Manischewitz, L. R. King, S. J. Snodgrass, J. Parrish, P. Markham, M. Sowers, D. Martin, M. G. Lewis, J. A. Berzofsky, I. M. Belyakov, B. Moss, J. Tartaglia, M. Bray, V. Hirsch, H. Golding, and G. Franchini. 2003. Modeling a safer smallpox vaccination regimen, for human immunodeficiency virus type 1-infected patients, in immunocompromised macaques. *J. Infect. Dis.* 188:1181-1191.
13. Edghill-Smith, Y., M. Bray, C. A. Whitehouse, D. Miller, E. Mucker, J. Manischewitz, L. R. King, M. Robert-Guroff, A. Hryniewicz, D. Venzon, C. Meseda, J. Weir, A.

Nalca, V. Livingston, J. Wells, M. G. Lewis, J. Huggins, S. H. Zwiers, H. Golding, and G. Franchini. 2005. Smallpox Vaccine Does Not Protect Macaques with AIDS from a Lethal Monkeypox Virus Challenge. *J. Infect. Dis.* 191: 372-381.

14. Edghill-Smith, Y., H. Golding, J. Manischewitz, L. R. King, D. Scott, M. Bray, A. Nalca, J. W. Hooper, C. A. Whitehouse, J. E. Schmitz, K. A. Reimann, and G. Franchini. 2005. Smallpox vaccine-induced antibodies are necessary and sufficient for protection against monkeypox virus. *Nat. Med.* 11:740-747.

15. Fogg, C., S. Lustig, J. C. Whitbeck, R. J. Eisenberg, G. H. Cohen, and B. Moss. 2004. Protective immunity to vaccinia virus induced by vaccination with multiple recombinant outer membrane proteins of intracellular and extracellular virions. *J. Virol.* 78:10230-10237.

16. Galmiche, M. C., J. Goenaga, R. Wittek, and L. Rindisbacher. 1999. Neutralizing and protective antibodies directed against vaccinia virus envelope antigens. *Virology* 254:71-80.

17. Hooper, J. W., D. M. Custer, C. S. Schmaljohn, and A. L. Schmaljohn. 2000. DNA vaccination with vaccinia virus L1R and A33R genes protects mice against a lethal poxvirus challenge. *Virology* %20; 266:329-339.

18. Fang, M., H. Cheng, Z. Dai, Z. Bu, and L. J. Sigal. 2006. Immunization with a single extracellular enveloped virus protein produced in bacteria provides partial protection from a lethal orthopoxvirus infection in a natural host. *Virology.* 345:231-243.

19. Smith, G. L. and M. Law. 2004. The exit of vaccinia virus from infected cells. *Virus Res.* 106:189-197.

20. Kulesh, D. A., R. O. Baker, B. M. Loveless, D. Norwood, S. H. Zwiers, E. Mucker, C. Hartmann, R. Herrera, D. Miller, D. Christensen, L. P. Wasieloski, Jr., J. Huggins, and P. B. Jahrling. 2004. Smallpox and pan-Orthopox Virus Detection by Real-Time 3'-Minor Groove Binder TaqMan Assays on the Roche LightCycler and the Cepheid Smart Cycler Platforms. *J. Clin. Microbiol.* 42:601-609.

21. Manischewitz, J., L. R. King, N. A. Bleckwenn, J. Shiloach, R. Taffs, M. Merchlinsky, N. Eller, M. G. Mikolajczyk, D. J. Clanton, T. Monath, R. A. Weltzin, D. E. Scott, and H. Golding. 2003. Development of a novel vaccinia-neutralization assay based on reporter-gene expression. *J. Infect. Dis.* 188:440-448.

22. Chakrabarti, S., J. R. Sisler, and B. Moss. 1997. Compact, synthetic, vaccinia virus early/late promoter for protein expression. *Biotechniques.* 23:1094-1097.

23. Hooper, J. W., D. M. Custer, and E. Thompson. 2003. Four-gene-combination DNA vaccine protects mice against a lethal vaccinia virus challenge and elicits appropriate antibody responses in nonhuman primates. *Virology* 306:181-195.

24. Boyce, T. G., W. C. Gruber, S. D. Coleman-Dockery, E. C. Sannella, G. W. Reed, M. Wolff, and P. F. Wright. 1999. Mucosal immune response to trivalent live attenuated intranasal influenza vaccine in children. *Vaccine.* %20; 18:82-88.

25. Zaucha, G. M., P. B. Jahrling, T. W. Geisbert, J. R. Swearengen, and L. Hensley. 2001. The pathology of experimental aerosolized monkeypox virus infection in cynomolgus monkeys (*Macaca fascicularis*). *Lab Invest.* 81:1581-1600.

26. Aldaz-Carroll, L., J. C. Whitbeck, d. L. Ponce, H. Lou, L. Hirao, S. N. Isaacs, B. Moss, R. J. Eisenberg, and G. H. Cohen. 2005. Epitope-mapping studies define two major neutralization sites on the vaccinia virus extracellular enveloped virus glycoprotein B5R. *J. Virol.* 79:6260-6271.

27. Engelstad, M., S. T. Howard, and G. L. Smith. 1992. A constitutively expressed vaccinia gene encodes a 42-kDa glycoprotein related to complement control factors that forms part of the extracellular virus envelope. *Virology* 188:801-810.

28. Law, M. and G. L. Smith. 2001. Antibody neutralization of the extracellular enveloped form of vaccinia virus. *Virology* 280:132-142.

29. Kemper, A. R., M. M. Davis, and G. L. Freed. 2002. Expected adverse events in a mass smallpox vaccination campaign. *Eff. Clin. Pract.* 5:84-90.

30. Osterhaus, A. D., C. A. van Baalen, R. A. Gruters, M. Schutten, C. H. Siebelink, E. G. Hulskotte, E. J. Tijhaar, R. E. Randall, G. van Amerongen, A. Fleuchaus, V. Erfle, and G. Sutter. 1999. Vaccination with Rev and Tat against AIDS. *Vaccine* 17:2713-2714.

31. Snyder, J. T., I. M. Belyakov, A. Dzutsev, F. Lemonnier, and J. A. Berzofsky. 2004. Protection against lethal vaccinia virus challenge in HLA-A2 transgenic mice by immunization with a single CD8+ T-cell peptide epitope of vaccinia and variola viruses. *J. Virol.* 78:7052-7060.

32. Wyatt, L. S., P. L. Earl, L. A. Eller, and B. Moss. 2004. Highly attenuated smallpox vaccine protects mice with and without immune deficiencies against pathogenic vaccinia virus challenge. *Proc. Natl. Acad. Sci. U.S.A* 101:4590-4595.

33. Chen, Z., P. Earl, J. Americo, I. Damon, S. K. Smith, Y. H. Zhou, F. Yu, A. Sebrell, S. Emerson, G. Cohen, R. J. Eisenberg, J. Svitel, P. Schuck, W. Satterfield, B. Moss, and R. Purcell. 2006. Chimpanzee/human mAbs to vaccinia virus B5 protein neutralize vaccinia and smallpox viruses and protect mice against vaccinia virus. *Proc. Natl. Acad. Sci. U.S.A.* 103:1882-1887.

34. Moller-Larsen, A. and S. Haahr. 1978. Humoral and cell-mediated immune responses in humans before and after revaccination with vaccinia virus. *Infect. Immun.* 19:34-39.

35. Saha, S, and G. P. S. Raghava. 2004. BcePred: Prediction of continuous B-cell epitopes in antigenic sequences using physico-chemical properties. In *ICARIS* 2004, *LNCS* 3239. G. Nicosia, V. Cutello, P. J. Bentley, and J. Timis, eds. Springer, pp. 197-204.

The invention claimed is:

1. A method for inducing in a subject a protective immune response against poxvirus, comprising the steps of
   (a) administering to said subject an immunologically effective amount of a nucleic acid vaccine comprising the poxvirus nucleic acids of (1) a nucleic acid encoding L1R or its ortholog (2) a nucleic acid encoding A33R or its ortholog, (3) a nucleic acid encoding A27L or its ortholog, and (4) a nucleic acid encoding B5R or its ortholog,
   (b) subsequently administering to said subject an immunologically effective amount of a protein vaccine comprising the purified recombinant poxvirus proteins or peptides of
      (i) a protein or peptide encoded by the open reading frame of the monkeypox ortholog L1R gene or its ortholog,
      (ii) a protein or peptide encoded by the open reading frame of the monkeypox ortholog A27L gene or its ortholog,
      (iii) a protein or peptide encoded by the open reading frame of the monkeypox ortholog A33R gene or its ortholog, and
      (iv) a protein or peptide encoded by the open reading frame of the monkeypox ortholog B5R gene or its ortholog, and an adjuvant; and
   (c) subsequently administering to said subject a second immunologically effective amount of a protein vaccine comprising the purified recombinant poxvirus proteins or peptides of
      (i) a protein or peptide encoded by the open reading frame of the monkeypox ortholog L1R gene or its ortholog,
      (ii) a protein or peptide encoded by the open reading frame of the monkeypox ortholog A27L gene or its ortholog,
      (iii) a protein or peptide encoded by the open reading frame of the monkeypox ortholog A33R gene or its ortholog, and (iv) a protein or peptide encoded by the open reading frame of the monkeypox ortholog B5R gene or its ortholog,
so as to induce a protective immune response against poxvirus in the subject.

2. The method of claim 1 for inducing in a subject an immune response against poxvirus, wherein the orthologs in (a) are derived from an orthopoxvirus selected from the group consisting of: camelpox virus, ectromelia virus, raccoon poxvirus, skunk poxvirus, Tatera poxvirus, Uasin Gishu virus, Volepox virus, variola virus, vaccinia virus, monkeypox virus, gerbilpox and cowpox virus, or genetically engineered versions thereof.

3. The method of claim 1 for inducing in a subject an immune response against poxvirus, wherein the orthologs of (b) and (c) are derived from an orthopoxvirus selected from the group consisting of: camelpox virus, ectromelia virus, raccoon poxvirus, skunk poxvirus, Tatera poxvirus, Uasin Gishu virus, Volepox variola virus, vaccinia virus, monkeypox virus, gerbilpox and cowpox virus, or genetically engineered versions thereof.

4. The method of claim 3 for inducing in a subject an immune response against poxvirus, wherein the orthologs are purified recombinant monkeypox virus proteins or peptides selected from the group consisting of a protein or peptide encoded by the open reading frame of the monkeypox ortholog M1R gene, a protein or peptide encoded by the open reading frame of the monkeypox ortholog A35R gene, a protein or peptide encoded by the open reading frame of the monkeypox ortholog A29L gene, a protein or peptide encoded by the open reading frame of the monkeypox ortholog B6R gene.

5. The method of claim 1 for inducing in a subject an immune response against poxvirus, wherein the nucleic acid vaccine is administered to the subject by intramuscular injection, intradermal injection, gene gun, electroporation, or biojector.

6. The method of claim 1 for inducing in a subject an immune response against poxvirus, wherein the protein vaccine is administered to the subject by intramuscular injection, intradermal injection, gene gun or electroporation.

7. The method of claim 1, wherein the protein of (b) is administered a minimum of a week following the administering of the nucleic acid of (a).

8. The method of claim 1 for inducing in a subject an immune response against poxvirus wherein said poxvirus protected against is an Orthopoxvirus chosen from the group consisting of: camelpox virus, ectromelia virus, raccoon poxvirus, skunk poxvirus, Tatera poxvirus, Uasin Gishu virus, Volepox virus variola virus, vaccinia virus, monkeypox virus, gerbilpox, and cowpox virus or genetically engineered versions thereof.

9. The method of claim 1 for inducing in a subject an immune response against poxvirus, wherein the nucleic acid vaccine is administered in a dosage range of between 50 micrograms and 1 milligram.

10. The method of claim 1 for inducing in a subject an immune response against poxvirus, wherein the protein of (b) is administered in a dosage range of between 50 micrograms and 1 milligram.

11. The method of claim 1 for inducing in a subject an immune response against poxvirus, wherein the protein of (c) is administered in a dosage range of between 50 micrograms and 1 milligram.

12. The method of claim 1 for inducing in a subject an immune response against poxvirus, wherein the nucleic acid vaccine comprises
a carrier particle having a nucleic acid sequence coated thereon comprising a promoter operative in the cells of a mammal and a protein coding region encoding for the poxvirus antigen L1R antigen or its ortholog,
a carrier particle having a nucleic acid sequence coated thereon comprising a promoter operative in the cells of a mammal and a protein coding region encoding for the poxvirus antigen A33R antigen or its ortholog,
a carrier particle having a nucleic acid sequence coated thereon comprising a promoter operative in the cells of a mammal and a protein coding region encoding for the poxvirus antigen A27L antigen or its ortholog, and
a carrier particle having a nucleic acid sequence coated thereon comprising a promoter operative in the cells of a mammal and a protein coding region encoding for the poxvirus antigen B5R antigen or its ortholog.

13. The method of claim 1, wherein the nucleic acid vaccine and the protein vaccine are administered to the subject subsequent to the subject's exposure to a poxvirus.

14. The method of claim 1, wherein the protein vaccine is administered in a cluster dosing regimen.

* * * * *

SEQUENCE LISTING

```
<160> NUMBER OF SEQ ID NOS: 35

<210> SEQ ID NO 1
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1
tcgtcgtttt gtcgttttct cgtt                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcgtcgtttt gtcgttttgt cgtt                                              24

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gatgatgcaa ctctatcatg ta                                                22

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtataattat caaaatacaa gacgtc                                            26

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
agtgcttggt ataaggag                                                     18

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatatacata tggacggaaa ctcttttccc cggagat                                37

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 7
ctcgagtgcg gccgcctcat agggacgccg tccagtctgt acat            44

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatatacata tgaatcaatg catgtctgct aacg                        34

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcgagtgcg gccgctgtac aaaaatactt tctaacttct tgtgatacat       50

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagatatata catatgaaaa cgatttccgt tgttacgttg ttatg            45

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctcgagtgc ggccgcatga taagttgctt ctaacgattc t                41

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagatataca tatggcagca agcatacaga cgactgtgaa                  40

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcgagtgcg gccgcaaact gaactcctgt accagcaact t                    41

<210> SEQ ID NO 14
<211> LENGTH: 16
<212> TYPE: PRT
<213> ORGANISM: Monkeypox virus

<400> SEQUENCE: 14

Asp Ser Gly Tyr His Ser Leu Asp Pro Asn Ala Val Cys Glu Thr Asp
 1               5                  10                  15

<210> SEQ ID NO 15
<211> LENGTH: 16
<212> TYPE: PRT
<213> ORGANISM: Vaccinia virus

<400> SEQUENCE: 15

Asp Gln Gly Tyr His Ser Leu Asp Pro Asn Ala Val Cys Glu Thr Asp
 1               5                  10                  15

<210> SEQ ID NO 16
<211> LENGTH: 16
<212> TYPE: PRT
<213> ORGANISM: Variola virus

<400> SEQUENCE: 16

Asp Ser Gly Tyr Tyr Ser Leu Asp Pro Asn Ala Val Cys Glu Thr Asp
 1               5                  10                  15

<210> SEQ ID NO 17
<211> LENGTH: 16
<212> TYPE: PRT
<213> ORGANISM: Ectromelia virus

<400> SEQUENCE: 17

Asp Gln Gly Tyr His Ser Leu Asp Pro Asn Ala Val Cys Glu Thr Asp
 1               5                  10                  15

<210> SEQ ID NO 18
<211> LENGTH: 16
<212> TYPE: PRT
<213> ORGANISM: Cowpox virus

<400> SEQUENCE: 18

Asp Gln Gly Tyr His Ser Leu Asp Pro Asn Ala Val Cys Glu Thr Asp
 1               5                  10                  15

<210> SEQ ID NO 19
<211> LENGTH: 16
<212> TYPE: PRT
<213> ORGANISM: Rabbitpox virus

<400> SEQUENCE: 19

Asp Gln Gly Tyr His Ser Ser Asp Pro Asn Ala Val Cys Glu Thr Asp
 1               5                  10                  15

<210> SEQ ID NO 20
<211> LENGTH: 27
<212> TYPE: PRT
<213> ORGANISM: Monkeypox virus

<400> SEQUENCE: 20

Cys Val Arg Ser Asn Glu Glu Phe Asp Pro Val Asp Gly Pro Asp
1               5                   10                  15

Asp Glu Thr Asp Leu Ser Lys Leu Ser Lys Asp
            20                  25

<210> SEQ ID NO 21
<211> LENGTH: 27
<212> TYPE: PRT
<213> ORGANISM: Vaccinia virus

<400> SEQUENCE: 21

Cys Val Arg Ser Asn Lys Glu Phe Asp Pro Val Asp Asp Gly Pro Asp
1               5                   10                  15

Asp Glu Thr Asp Leu Ser Lys Leu Ser Lys Asp
            20                  25

<210> SEQ ID NO 22
<211> LENGTH: 27
<212> TYPE: PRT
<213> ORGANISM: Variola virus

<400> SEQUENCE: 22

Cys Ile Arg Ser Asn Glu Glu Phe Asp Pro Val Glu Asp Gly Pro Asp
1               5                   10                  15

Asp Glu Thr Asp Leu Ser Lys Leu Ser Lys Asp
            20                  25

<210> SEQ ID NO 23
<211> LENGTH: 27
<212> TYPE: PRT
<213> ORGANISM: Ectromelia virus

<400> SEQUENCE: 23

Cys Val Arg Ser Asn Glu Glu Phe Asp Pro Ile Asp Asp Asp Pro Asp
1               5                   10                  15

Asp Glu Thr Asp Leu Ser Lys Ile Ser Lys Asp
            20                  25

<210> SEQ ID NO 24
<211> LENGTH: 27
<212> TYPE: PRT
<213> ORGANISM: Cowpox virus

<400> SEQUENCE: 24

Cys Val Arg Ser Asn Glu Glu Phe Asp Leu Val Asp Asp Gly Pro Asp
1               5                   10                  15

Asp Glu Thr Asp Leu Ser Lys Ile Ser Lys Asp
            20                  25

<210> SEQ ID NO 25
<211> LENGTH: 27
<212> TYPE: PRT
<213> ORGANISM: Rabbitpox virus

<400> SEQUENCE: 25

Cys Val Arg Thr Asn Glu Glu Phe Asp Pro Val Asp Asp Gly Pro Asp
1               5                   10                  15

Asp Glu Thr Asp Leu Ser Lys Leu Ser Lys Asp
            20                  25

<210> SEQ ID NO 26
<211> LENGTH: 31

```
<212> TYPE: PRT
<213> ORGANISM: Monkeypox virus

<400> SEQUENCE: 26

Lys Glu Ser Cys Asn Gly Leu Tyr Tyr Gln Gly Ser Cys Tyr Ile Leu
 1               5                  10                  15

His Ser Asp Tyr Lys Ser Phe Glu Asp Ala Lys Ala Asn Cys Ala
            20                  25                  30

<210> SEQ ID NO 27
<211> LENGTH: 31
<212> TYPE: PRT
<213> ORGANISM: Vaccinia virus

<400> SEQUENCE: 27

Lys Glu Ser Cys Asn Gly Leu Tyr Tyr Gln Gly Ser Cys Tyr Ile Leu
 1               5                  10                  15

His Ser Asp Tyr Gln Leu Phe Ser Asp Ala Lys Ala Asn Cys Thr
            20                  25                  30

<210> SEQ ID NO 28
<211> LENGTH: 31
<212> TYPE: PRT
<213> ORGANISM: Variola virus

<400> SEQUENCE: 28

Gln Glu Ser Cys Asn Gly Leu Tyr Tyr Gln Gly Ser Cys Tyr Ile Phe
 1               5                  10                  15

His Ser Asp Tyr Gln Leu Phe Ser Asp Ala Lys Ala Asn Cys Ala
            20                  25                  30

<210> SEQ ID NO 29
<211> LENGTH: 31
<212> TYPE: PRT
<213> ORGANISM: Camelpox virus

<400> SEQUENCE: 29

Lys Glu Ser Cys Asn Gly Leu Tyr Tyr Gln Gly Ser Cys Tyr Ile Phe
 1               5                  10                  15

His Ser Asp Tyr Gln Leu Phe Ser Asp Ala Lys Ala Asn Cys Thr
            20                  25                  30

<210> SEQ ID NO 30
<211> LENGTH: 23
<212> TYPE: PRT
<213> ORGANISM: Monkeypox virus

<400> SEQUENCE: 30

Leu Ser Ala Ala Thr Glu Thr Tyr Ser Gly Leu Thr Pro Glu Gln Lys
 1               5                  10                  15

Ala Tyr Val Pro Ala Met Phe
            20

<210> SEQ ID NO 31
<211> LENGTH: 23
<212> TYPE: PRT
<213> ORGANISM: Vaccinia virus

<400> SEQUENCE: 31

Leu Ser Ala Ala Thr Glu Thr Tyr Ser Gly Leu Thr Pro Glu Gln Lys
 1               5                  10                  15

Ala Tyr Val Pro Ala Met Phe
            20
```

```
<210> SEQ ID NO 32
<211> LENGTH: 23
<212> TYPE: PRT
<213> ORGANISM: Variola virus

<400> SEQUENCE: 32

Leu Ser Ala Ala Thr Glu Thr Tyr Ser Gly Leu Thr Pro Glu Gln Lys
 1               5                  10                  15

Ala Tyr Val Pro Ala Met Phe
            20

<210> SEQ ID NO 33
<211> LENGTH: 19
<212> TYPE: PRT
<213> ORGANISM: Monkeypox virus

<400> SEQUENCE: 33

Tyr Gly Ala Pro Gly Ser Pro Thr Asn Leu Glu Phe Ile Asn Thr Gly
 1               5                  10                  15

Ser Ser Lys

<210> SEQ ID NO 34
<211> LENGTH: 19
<212> TYPE: PRT
<213> ORGANISM: Vaccinia virus

<400> SEQUENCE: 34

Tyr Gly Ala Pro Gly Ser Pro Thr Asn Leu Glu Phe Ile Asn Thr Gly
 1               5                  10                  15

Ser Ser Lys

<210> SEQ ID NO 35
<211> LENGTH: 19
<212> TYPE: PRT
<213> ORGANISM: Variola virus

<400> SEQUENCE: 35

Tyr Gly Ala Pro Gly Ser Pro Thr Asn Leu Glu Phe Ile Asn Thr Gly
 1               5                  10                  15

Ser Ser Lys
```